(12) United States Patent
Lang et al.

(10) Patent No.: US 12,409,289 B2
(45) Date of Patent: Sep. 9, 2025

(54) PATIENT INTERFACE, SEAL FORMING STRUCTURE AND METHOD OF MANUFACTURING OF THE SAME

(71) Applicant: ResMed Pty Ltd, Bella Vista (AU)

(72) Inventors: Bernd Christoph Lang, Graefelfing (DE); Andreas Kirchberger, Miesbach (DE); Johannes Nickol, Neukenroth (DE); Jens Rothfuss, Unterschleissheim (DE); Johann Sebastian Burz, Germaringen (DE); Robert Eibl, Bad Toelz (DE); Christian Bayer, Penzberg (DE)

(73) Assignee: ResMed Pty Ltd, Bella Vista (AU)

( * ) Notice: Subject to any disclaimer, the term of this patent is extended or adjusted under 35 U.S.C. 154(b) by 648 days.

(21) Appl. No.: 17/668,559

(22) Filed: Feb. 10, 2022

(65) Prior Publication Data

US 2022/0226594 A1    Jul. 21, 2022

Related U.S. Application Data

(63) Continuation of application No. 15/063,709, filed on Mar. 8, 2016, now Pat. No. 11,278,691.

(30) Foreign Application Priority Data

Mar. 16, 2015    (EP) .................................... 15159272

(51) Int. Cl.
*A61M 16/06* (2006.01)
*A61M 16/00* (2006.01)
(Continued)

(52) U.S. Cl.
CPC .... *A61M 16/0616* (2014.02); *A61M 16/0057* (2013.01); *A61M 16/06* (2013.01);
(Continued)

(58) Field of Classification Search
CPC ............. A61M 16/0616; A61M 16/06; A61M 2205/0216; A61M 2207/00;
(Continued)

(56) References Cited

U.S. PATENT DOCUMENTS

| | | | |
|---|---|---|---|
| 6,397,847 B1 * | 6/2002 | Scarberry | A61M 16/0605 2/430 |
| 2008/0052450 A1 | 2/2008 | Buer | |
| 2008/0053450 A1 * | 3/2008 | Van Kerkwyk | A61M 16/06 128/205.25 |

(Continued)

FOREIGN PATENT DOCUMENTS

| | | |
|---|---|---|
| FR | 2 944 211 | 10/2010 |
| FR | 2 944 211 A1 | 10/2010 |

(Continued)

OTHER PUBLICATIONS

EP Search Report for EP15159272.2 dated Jul. 3, 2015, five pages.
Extended European Search Report dated Feb. 7, 2023 issued in European Application No. 22184421.0 (8 pages).

*Primary Examiner* — Timothy A Stanis
(74) *Attorney, Agent, or Firm* — Nixon & Vanderhye P.C.

(57) ABSTRACT

The present specification is directed a method manufacturing a patient interface for treatment of sleep disordered breathing using air pressure by delivery of air to a patient's airway. The method includes locating a shell, a first sub section of a seal forming structure, and a first section of the seal forming structure in a tool. The first sub section includes a groove. The first section is constructed from a thermoformable material. The method further includes introducing a moulding material to the tool and overmolding the shell, the first sub section, and the first section. The moulded material forms a second sub section of the seal forming structure that connects the first sub section to the shell and fully encloses the first section within the groove.

18 Claims, 19 Drawing Sheets

(51) Int. Cl.
    *B29C 65/70* (2006.01)
    *B29C 65/72* (2006.01)
    *B29K 83/00* (2006.01)
    *B29L 31/00* (2006.01)

(52) U.S. Cl.
    CPC .............. *B29C 65/70* (2013.01); *B29C 65/72* (2013.01); *A61M 2016/0661* (2013.01); *A61M 2205/0216* (2013.01); *A61M 2207/00* (2013.01); *B29K 2083/00* (2013.01); *B29L 2031/753* (2013.01)

(58) Field of Classification Search
    CPC .......... A61M 16/0622; A61M 16/0605; B29C 65/70; B29C 65/72; B29K 2083/00; B29L 2031/753
    See application file for complete search history.

(56) References Cited

U.S. PATENT DOCUMENTS

| | | | |
|---|---|---|---|
| 2011/0088699 A1* | 4/2011 | Skipper | A61M 16/06 128/206.26 |
| 2015/0374945 A1 | 12/2015 | Anthony | |
| 2016/0271350 A1 | 9/2016 | Lang et al. | |
| 2017/0151407 A1* | 6/2017 | Kirchberger | A61M 16/0605 |
| 2020/0114107 A1* | 4/2020 | Guney | A61M 16/0683 |

FOREIGN PATENT DOCUMENTS

| | | |
|---|---|---|
| WO | WO 2004/007010 | 1/2004 |
| WO | WO 2007/104042 | 9/2007 |
| WO | WO 2009/062265 | 5/2009 |
| WO | 2010/125074 A1 | 11/2010 |
| WO | 2014/125066 A1 | 8/2014 |

\* cited by examiner

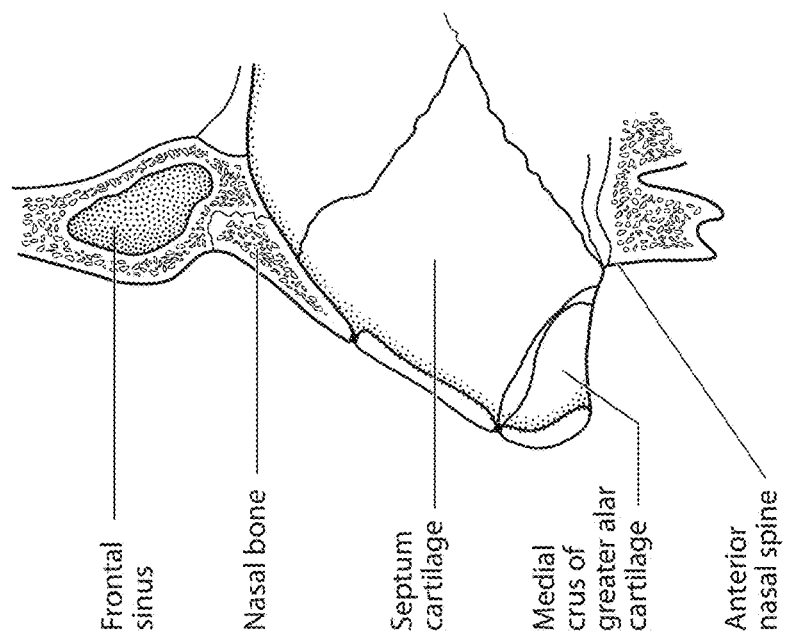
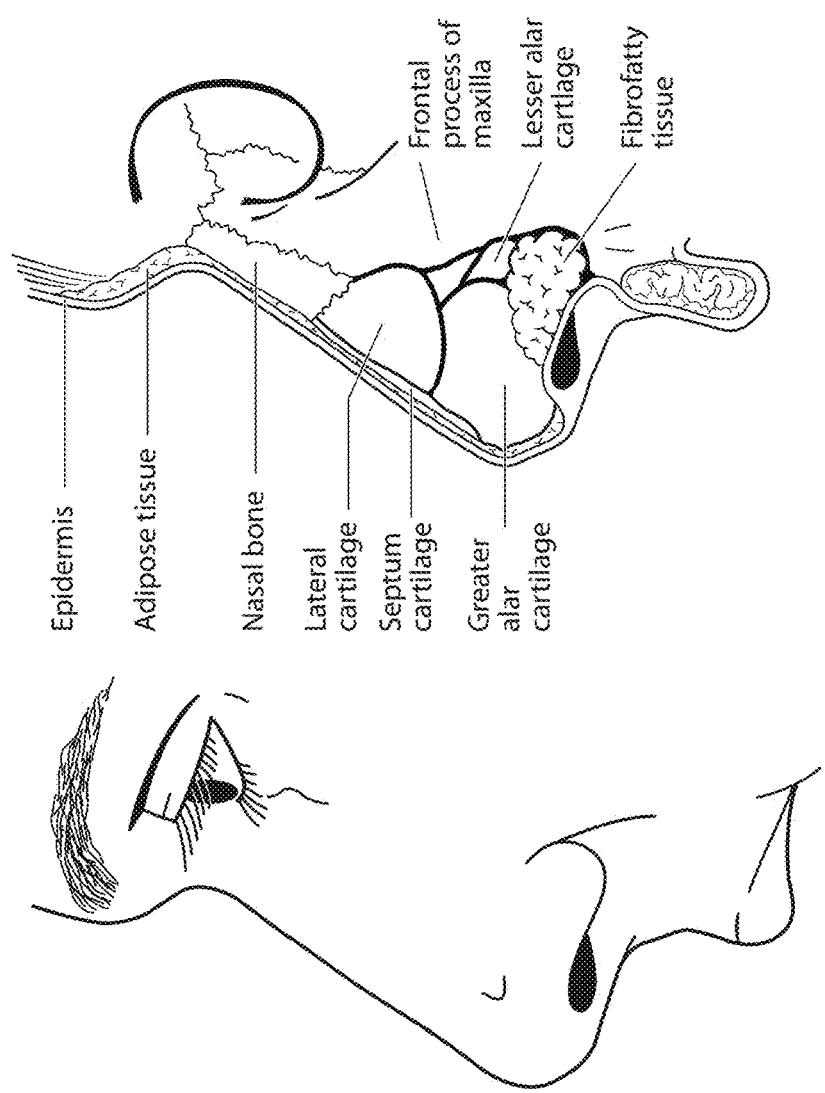
FIG. 2G  FIG. 2H  FIG. 2I

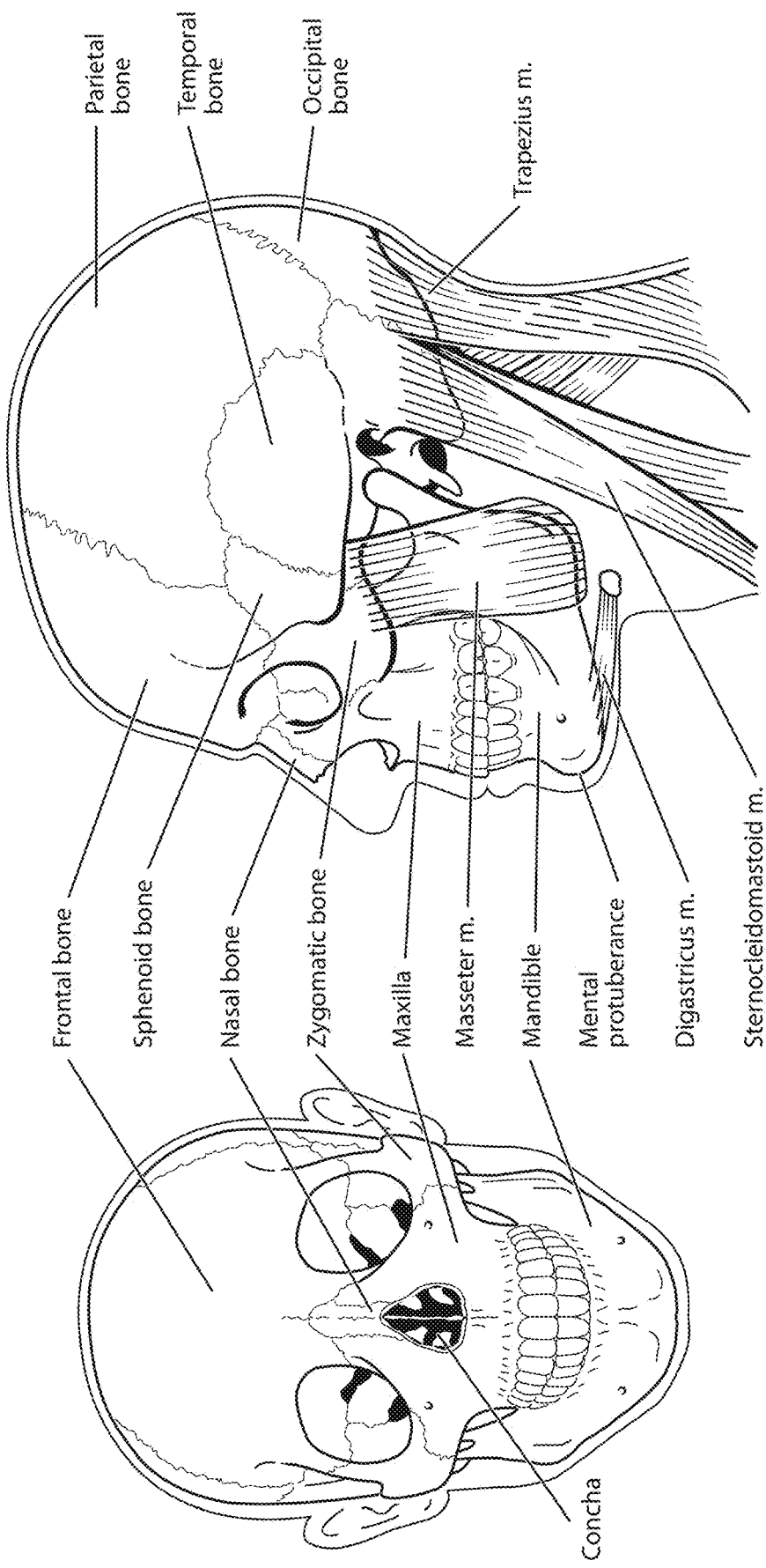

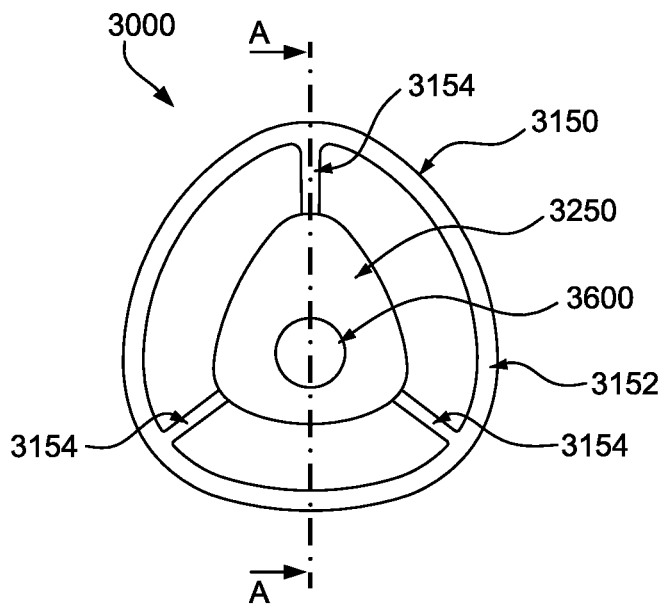
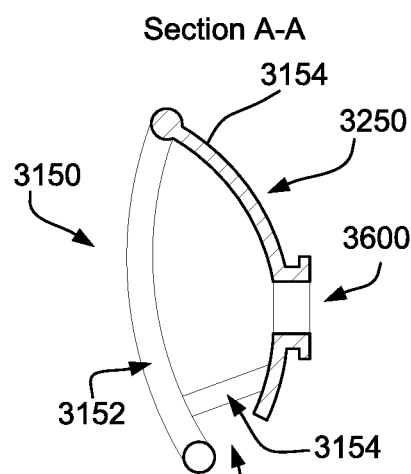
Fig. 7a
Fig. 7b
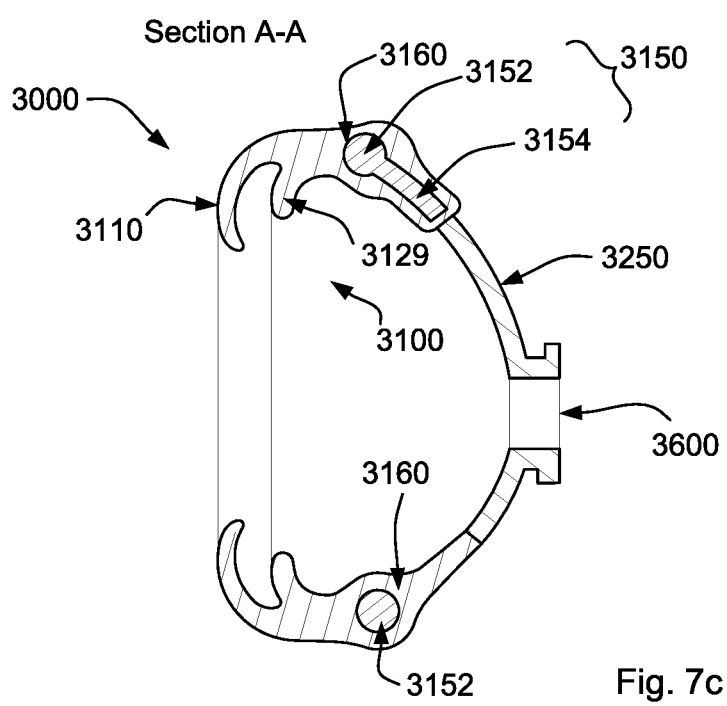
Fig. 7c

PATIENT INTERFACE, SEAL FORMING STRUCTURE AND METHOD OF MANUFACTURING OF THE SAME

This is a continuation of U.S. application Ser. No. 15/063,709, filed Mar. 8, 2016, now allowed, which claims priority to EP Patent Application No. 15159272.2 filed Mar. 16, 2015, the entire contents of which is hereby incorporated by reference.

1 BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use. In particular, the present technology is directed to a patient interface and a seal forming structure for such a patient interface, as well as manufacturing methods of the same.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchairbound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT" nasal pillows mask, SWIFT" II nasal pillows mask, SWIFT™ LT nasal pillows mask, SWIFT™ FX nasal pillows mask and MIRAGE LIBERTY' full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY" full-face mask); International Patent Application WO 2009/052,560 (describing amongst other things aspects of the ResMed Limited SWIFT" FX nasal pillows).

1.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.1.3 Vent Technologies

Some forms of patient interface systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed-partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2: 2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO3744 in CPAP mode at 10 cmH$_2$O)Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

1.2.3.2 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the lower jaw or mandible. The upper and lower splints are connected together laterally via a pair of connecting rods. The pair of connecting rods is fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

1.2.3.3 Patient Interfaces and Seal Forming Structures of Interest for the Present Technology Turning back to the seal forming structures, there are commonly associated the following challenges: At the one hand, a substantially air tight seal should be provided by the seal forming structure. In this regard, it may desirable that the seal forming structure is securely pressed onto the patient's face. On the other hand, patient comfort is also desirable. In this regard, it is not desirable to firmly press the seal forming structure against the patient's face, as this may result in pressure marks, pressure sores and pain of the patient; in particular, as the respective devices are typically worn for several hours, e.g. the complete duration of the night's sleep. Ultimately, this may also result in the patient not being compliant with the therapy. That is, it is generally a desire to provide a seal forming structure, which, at the same time, firmly seals an interior of the patient interface from an exterior of the patient interface and, is also comfortable for the patient to wear.

2 BRIEF SUMMARY OF THE TECHNOLOGY

In order to achieve this, it may be desirable to provide a seal forming structure well fitted to the patient. It may thus be a first object of the present technology to provide a seal forming structure, as well as a corresponding patient interface, overcoming or at least alleviating the problems associated with the prior art. In other words, it may be an object of the present technology to provide a seal forming structure and a respective patient interface having improved characteristics as regards sealing capabilities and patient comfort.

It is a further object of the present technology to also provide methods of manufacturing of the respective devices.

These objects are fulfilled by the present technology.

According to one aspect of the present technology, a user formable element is provided for a patient interface. Such patient interface is preferably adapted and suitable for treatment of disordered breathing sleep using air pressure and for delivering air, particularly pressurized air, to a patient's airway. For example, the user formable element may be a seal forming structure. In one embodiment, the user formable element comprises, in particular, a section of a thermo-formable material. That is a material having a relatively low softening or transition temperature, such as polycaprolactone (PCL). Such an element can then be fitted by a user to the individual physiological facial characteristics to fit the patient interface or at least the user formable element to the individual patient. This may provide more comfortable seating and/or improved sealing of the interface on a patient's face, particularly during therapy of sleep disordered breathing using air pressure.

The shaping of the formable material is intended to occur following known procedures for such materials, such as heating in warm water, by infrared radiation, microwave radiation or other means of heating available in the user's household.

The thermo-formable material has properties enabling it to soften when exposed to increased temperatures, such as 40° C.-100° C., and to solidify again as the temperature drops below a certain threshold. The transition temperature of the material may be sufficiently low so that sustained contact with the patient's face during the forming stage is advantageously possible without, e.g., causing pain or skin damage due to the material's temperature.

The user may heat either only the user formable element, such as the seal forming structure, and/or the entire mask system, then apply the heated section to his or her face so that it adapts to the physical characteristics. Finally, the user formable element is cooled again so that it retains the new, customized shape which now effectively corresponds to the patient's physiognomy. In this context, it is to be noted that the material is not necessarily actively cooled, e.g. by commonly known measures, such as by immersion in a liquid or a gas of lower temperature, or by exposure to a cooling air flow or the like. The temperature drop below the transition temperature threshold may also occur due to passive cooling, i.e. passive heat dissipation due to the material cooling off by itself due to heat dissipation into ambient.

However, the material of user formable element, for example, PCL, may not suffice as a material for the seal forming structure, due to, for example, its handling issues, lack of softness, lack of elasticity, etc. In a preferred embodiment of the present technology, it is therefore intended to combine the user formable element with other materials, such a polycarbonate, polyamide, polybutylene terephthalate, and others. Furthermore, other known soft and elastic materials, such as silicone, thermoplastic elastomers, foams, and others, may also be used to produce the seal forming structure. The present technology may therefore improve the fit and functioning of existing respiratory masks and add the benefit of providing the user with means for adaptation to his individual physiognomy.

The advantages of the present technology include an improved mask fit and seal, improved comfort through individualized fit, reduction of pressure points and pressure sores. Furthermore, with the manufacturing methods disclosed herein, the devices may also be produced in an efficient manner.

The present technology is generally directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of one form of the present technology is a method of manufacturing apparatus.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

The present technology may also be described by way of one or more of the following numbered aspects:

1. A seal forming structure for a patient interface for treatment of sleep disordered breathing using air pressure, particularly by delivery of air to a patient's airway, wherein the seal forming structure comprises a first section of a thermoformable material and a second section of another material.

While it is preferred that the first section includes a thermoformable material and this embodiment is discussed in greater detail below, it is to be understood that the present technology is not limited to such materials. Instead, other user-formable materials may also be used—instead of applying heat to the user-formable material, it may also be possible that other measures are applied thereto to bring the material in a transition state (i.e. a state where the user may deform it). Non-limiting examples of bringing the material to the transition state include the application of pressure, force, humidity, voltage or current.

2. A seal forming structure according to the preceding aspect, wherein the first section is partially enclosed within the second sections, preferably on the side intended and adapted for sealing contact with a patient's face and is, preferably, completely enclosed within the second section.

3. A seal forming structure according to any of the preceding aspects, wherein the second section comprises a planar border section for connection to a platform region, preferably the platform region of a mask frame.

4. A seal forming structure according to any of the preceding aspects, wherein the second section comprises a sealing flange or membrane for sealing against a patient's face.

A sealing flange may also be referred to as a flat or finlike member for sealing against a patient's face. Alternatively, it may also be referred to as a sealing flap or membrane.

5. A seal forming structure according to the preceding aspect, wherein the second section further comprises a support flange or support rim. Such support flange or rim may also be referred to as an undercushion.

6. A seal forming structure according to any of the preceding aspects, wherein the seal forming structure comprises a perimeter and the first section runs along the entire perimeter of the seal forming structure.

7. A seal forming structure according to any of the aspects 1 to 5, wherein the seal forming structure comprises a perimeter and the first section does not run along the entire perimeter of the seal forming structure.

8. A seal forming structure according to any of the preceding aspects, wherein the amount of thermoformable material varies along the perimeter of the seal forming structure.

In other words, there are different amounts (i.e. areas) of thermoformable material in different cross sections along the perimeter. Such amounts may vary in thickness, width, or cross-sectional geometry.

9. A seal forming structure according to any of the preceding aspects, wherein the thermorformable material is polycaprolactone (PCL).

10. A seal forming structure according to any of the preceding aspects, wherein the material of the second section is an elastic material, such as silicone, a thermoplastic elastomer and/or a foam material.

When reference to silicone is made in this specification, in particular a synthetic rubber is meant. In this specification, a reference to silicone may be a reference to liquid silicone rubber (LSR) or a compression moulded silicone rubber (CMSR). Unless otherwise specified to the contrary, an exemplary form of LSR has a Shore A (or Type A) indentation hardness in the range of about 10 to 60, preferably 20 to 60, also preferably or about 35 to about 45 as measured, e.g., using ASTM D2240. Preferably, the reference to silicone does not include silicone gel.

11. A seal forming structure according to any of the preceding aspects, wherein the seal forming structure is a seal forming structure of a nasal mask or an oro-nasal mask.

12. A patient interface comprising a seal forming structure according to any of the preceding aspects.

13. A patient interface according to the preceding aspect, wherein the patient interface further comprises a shell.

14. A patient interface according to the preceding aspect, wherein the shell is formed of polycarbonate, polyamide and/or polybutylene terephthalate.

15. A patient interface according to any of the 3 preceding aspects, wherein the patient interface further comprises a platform region, wherein the seal forming structure is attached to the platform region, e.g. by means of an adhesive.

16. A patient interface according to the preceding aspect, wherein the patient interface further comprises a carrier portion comprising the platform region.

17. A patient interface according to the preceding aspect, wherein the carrier portion is generally T-shaped.

18. A patient interface according to any of the 2 preceding aspects, wherein the carrier portion is formed of the same material as the shell.

19. A patient interface according to any of preceding aspects 16 and 17, wherein the carrier portion is formed of another material than the shell, wherein preferably the material of the carrier portion is more flexible than the material of the shell.

20. A patient interface according to any of the 8 preceding aspects, wherein the patient interface further comprises a connection port for connection of a breathing gas line and/or a swivel elbow.

21. A patient interface according to any of the 9 preceding aspects, wherein the patient interface further comprises a vent for venting exhaled air.

22. A patient interface according to any of the 10 preceding aspects, wherein the patient interface is a nasal mask or an oro-nasal mask.

23. A patient interface according to the aspects 12 to 14, 20 to 22 when not dependent on aspects 2 and 15 to 19, wherein the first section is, in a cross sectional view, an elongated section, wherein a longitudinal end of the first section is connected to the shell, or frame structure, and the areas of the first section not being in contact with the shell are enclosed by the second section.

24. A patient interface according to the preceding aspect, wherein the longitudinal end of the first section is connected to the shell by means of an interface for a chemical bond, a moulded mechanical interlock or a mechanical interlock in the form of a snap-fit connection.

25. A patient interface according to any of the aspects 12 to 14 and 20 to 22, when not dependent on aspects 2 and 15 to 19, wherein the first section comprises a perimeter section and a plurality of web portions connecting the perimeter section to the shell.

26. A patient interface according to the preceding aspect, wherein the perimeter section is spaced at a distance of at least 10 mm to 60 mm from the shell.

27. A patient interface according to any of the 2 preceding aspects, wherein there are provided 3 or more web portions.

28. A patient interface according to any of the 3 preceding aspects, wherein there are provided 3 or more web portions, wherein the web portions are connected to the shell by means of an interface for a chemical bond, a moulded mechanical interlock or a mechanical interlock in the form of a snap-fit connection.

27. A patient interface according to any of the aspects 12 to 14 and 20 to 22, when not dependent on aspects 15 to 19, wherein the second section comprises different sub sections, wherein a first sub section includes a groove and wherein the first section is located in the groove by means of second sub section which also connects the seal forming structure to the shell.

28. A patient interface according to the preceding aspect, wherein the different sub sections of the second section are formed from the same material.

29. A patient interface according to the preceding aspect, wherein the material of the second section is silicone.

30. A patient interface according to aspect 27, wherein different sub sections of the second section are formed from different materials.

31. A seal forming structure for a patient interface for treatment of sleep disordered breathing using air pressure, particularly by delivery of air to a patient's airway, wherein the seal forming structure comprises a section of a material, said section including a groove for receiving a section of thermoformable material.

32. A seal forming structure according to the preceding aspect, wherein the seal forming structure includes any of the features recited in aspects 3 to 5 and 10 to 11.

33. A seal forming structure according to any of the two preceding aspects, wherein the groove runs along the entire perimeter of the seal forming structure.

34. A seal forming structure according to any of the aspects 31 to 32, wherein the groove does not run along the entire perimeter of the seal forming structure.

35. A seal forming structure according to the any of the 4 preceding aspect, wherein the groove is located such that the groove opens to the outside of the patient interface during use of the patient interface.

36. A seal forming structure according to any of the 5 preceding aspects, wherein the groove comprises at least one undercut, and preferably two undercuts, to retain the section of thermoformable material.

37. A seal forming structure according to any of the 6 preceding aspects further comprising a section of thermoformable material located in the groove, wherein the thermoformable material preferably is polycaprolactone.

38. A patient interface comprising a seal forming structure according to any of the 7 preceding aspects.

39. A patient interface according to the preceding aspect, wherein the patient interface includes the features recited in any of the aspects 13 to 22.

The present technology is also generally directed to methods for manufacturing a patient interface as described in any of the aspects 12 to 30 and 38 to 39.

40. Method of manufacturing a patient interface for treatment of sleep disordered breathing using air pressure, particularly by delivery of air to a patient's airway, the method comprising the steps:
connecting a section of thermoformable material onto a shell insert;
overmoulding at least the section of thermoformable material with a moulding material and thereby forming a seal forming structure.

41. Method according to the preceding aspect, wherein the method also comprises the step of inserting the mask shell insert and the section of thermoformable material into a moulding tool.

42. Method according to any of the 2 preceding aspects, wherein the moulding material is silicone.

43. Method according to any of the 3 preceding aspects, wherein the step of connecting the section of thermoformable material onto the mask shell insert comprises at least one of the following: chemically bonding, adhering and mechanically interlocking, e.g. by means of moulds or snap-fits, the two to one another.

44. Method according to any of the 4 preceding aspects, wherein the patient interface comprises any of the features recited in aspects 13 to 14 and 20 to 28.

45. Method according to any of the 5 preceding aspects, wherein the section of thermoformable material comprises a perimeter section and a plurality of web portions and wherein in the step of connecting the section of thermoformable material onto the shell insert, only the web portions are connected to the shell insert.

46. Method according to the preceding aspect, wherein in the overmoulding step, gaps between the shell insert and the perimeter section are filled by the moulding material.

47. Method of manufacturing a patient interface for treatment of sleep disordered breathing using air pressure, particularly by delivery of air to a patient's airway, the method comprising the steps of:
providing a shell insert, an insert for a first sub section of a seal forming structure, wherein the first sub section includes a groove, and a section of thermoformable material;
locating the provided structures in a tool such that the section of thermoformable material is located within the groove;
overmoulding the structures with a moulding material, such that the moulding material connects the shell insert, the first subsection and the section of thermoformable material.

48. Method according to the preceding aspect, wherein the moulding material is silicone.

49. Method according to any of the two preceding aspects further comprising the step of locating the section of thermoformable material in the groove, wherein this step includes at least one of the following steps:
casting, potting, dosing or moulding the section of thermoformable material in the groove.

50. Method according to any of the 3 preceding aspects, wherein the patient interface to be manufactured comprises any of the features recited in aspects 2, 4 to 22 and 27 to 30.
51. Method according to any of the 4 preceding aspects, wherein the tool is a tool having different tool sections, such as a fixed and a moveable tool section.
52. Method of manufacturing a patient interface for treatment of sleep disordered breathing using air pressure, particularly by delivery of air to a patient's airway, the method comprising the steps of:
providing a shell insert and a an insert for a section of a seal forming structure, wherein the insert for a section of the seal forming structure includes a groove;
moulding the inserts to one another with a moulding material.
53. Method of manufacturing according to the preceding aspect and further comprising the step of
locating a section of thermoformable material in the groove.
54. Method of manufacturing according to the preceding aspect, wherein the step of locating the section of thermoformable material in the groove includes a potting and/or dosing process.
55. Method of manufacturing according to any of the 3 preceding aspects, wherein silicone is used as a moulding material.
56. Method of manufacturing according to any of the 4 preceding aspects, wherein the patient interface comprises any of the features recited in aspects 2, 4 to 22 and 31 to 39.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1a shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

3.2 Respiratory System and Facial Anatomy

Figure 1A:
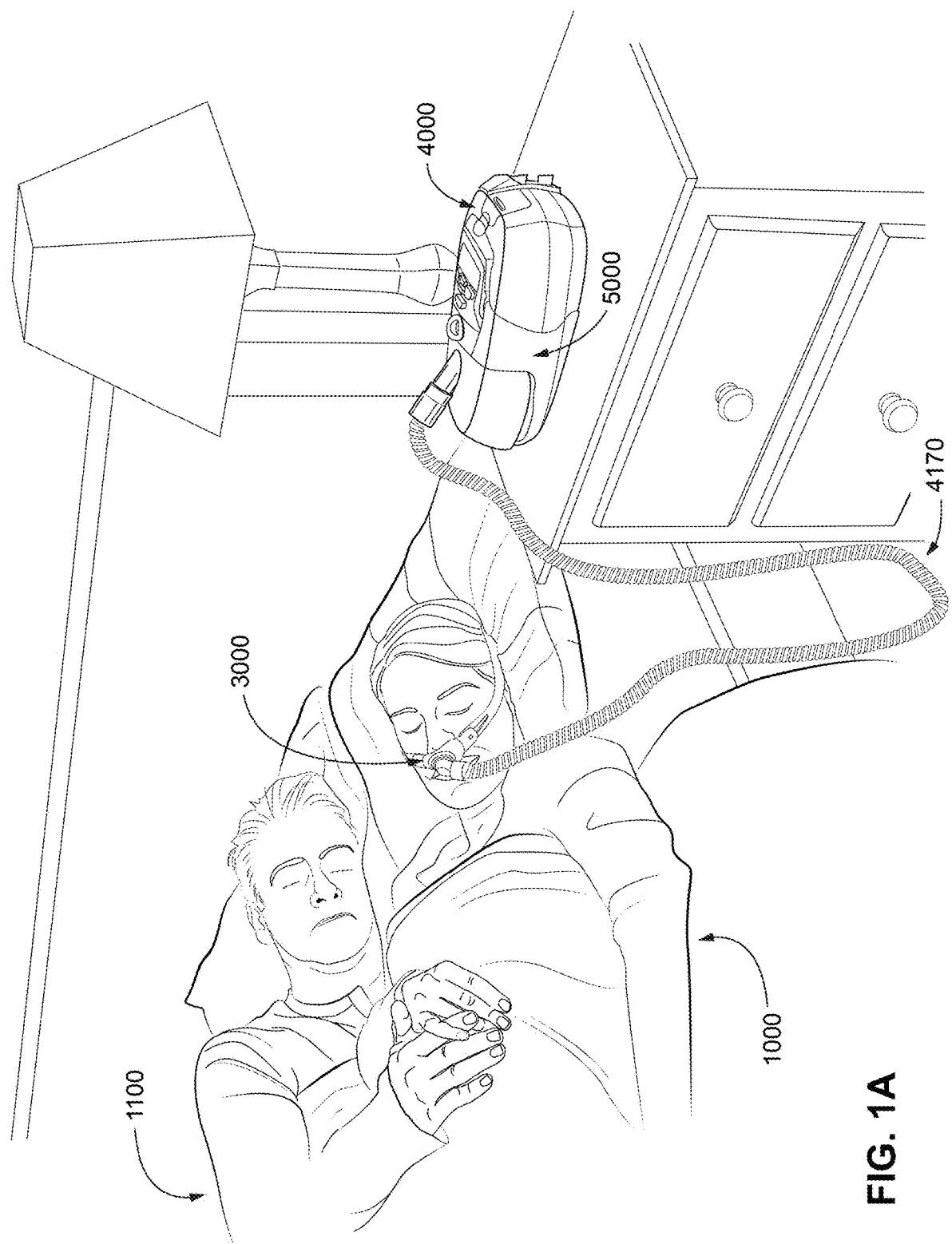
FIG. 1b shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1c shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
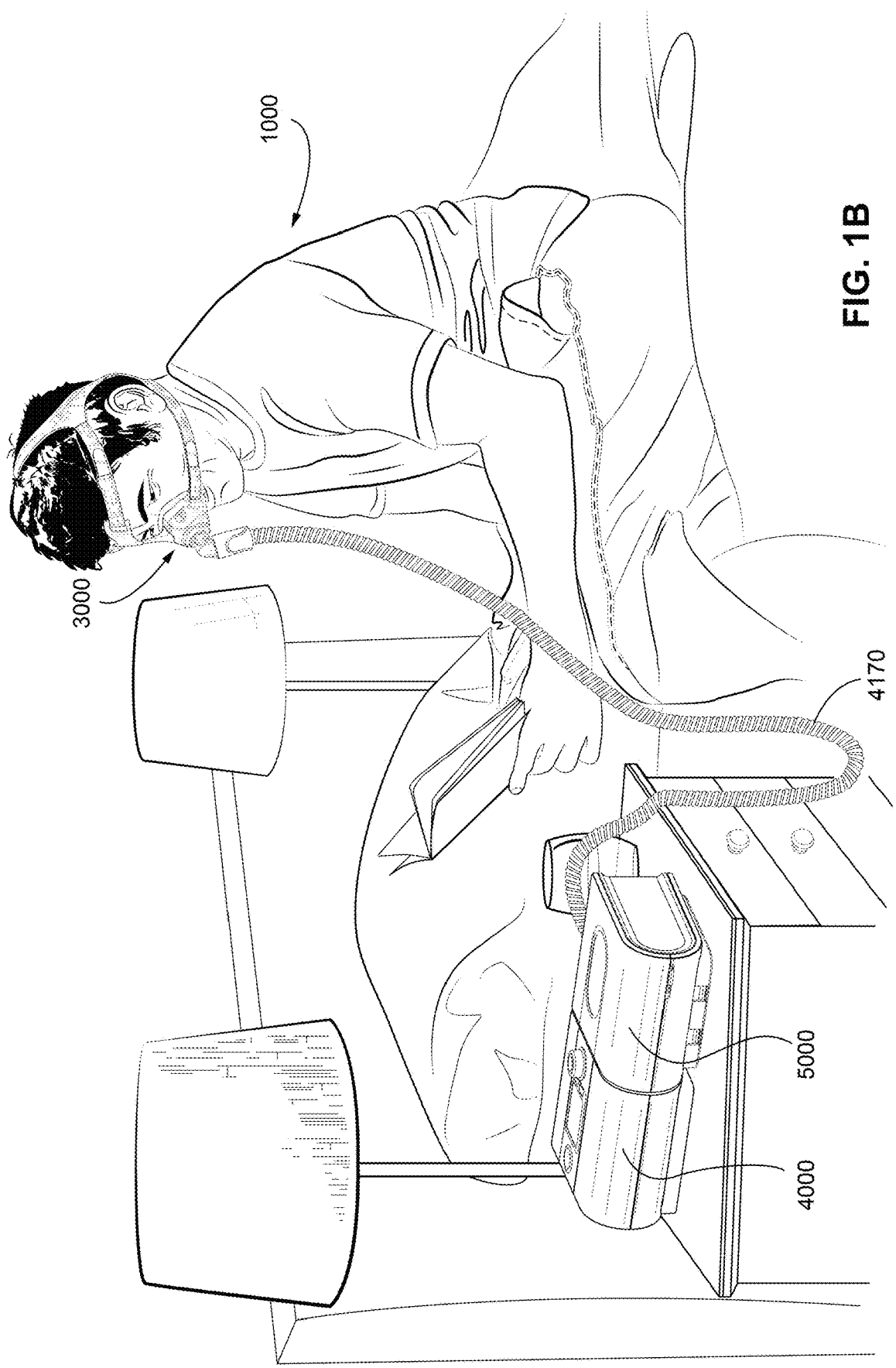
Figure 1C:
Figure 2A:
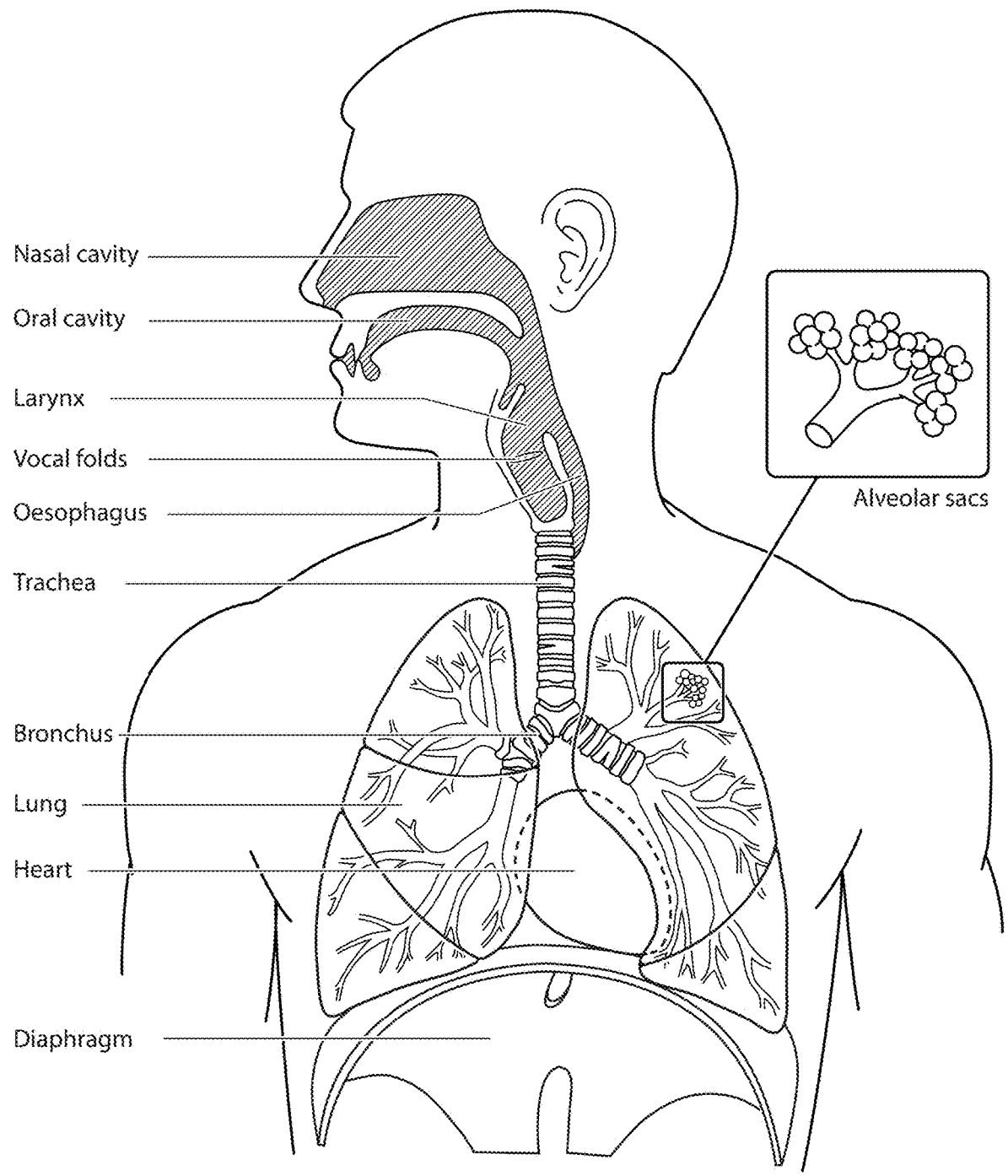

FIG. 2a shows an overview of a human respiratory system including the nasal and oral cavities, the larynx, vocal folds, oesophagus, trachea, bronchus, lung, alveolar sacs, heart and diaphragm.

Figure 2B:
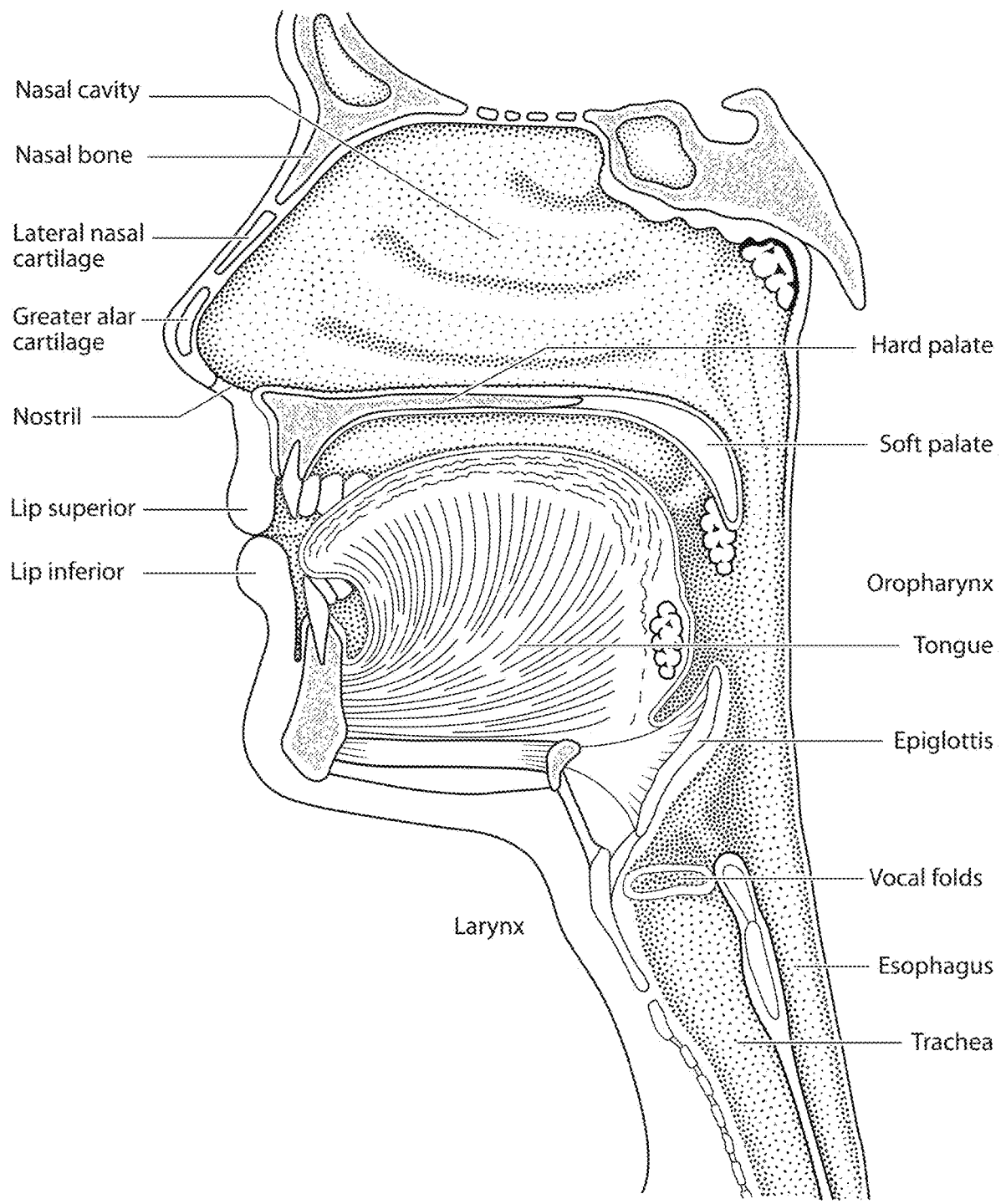

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
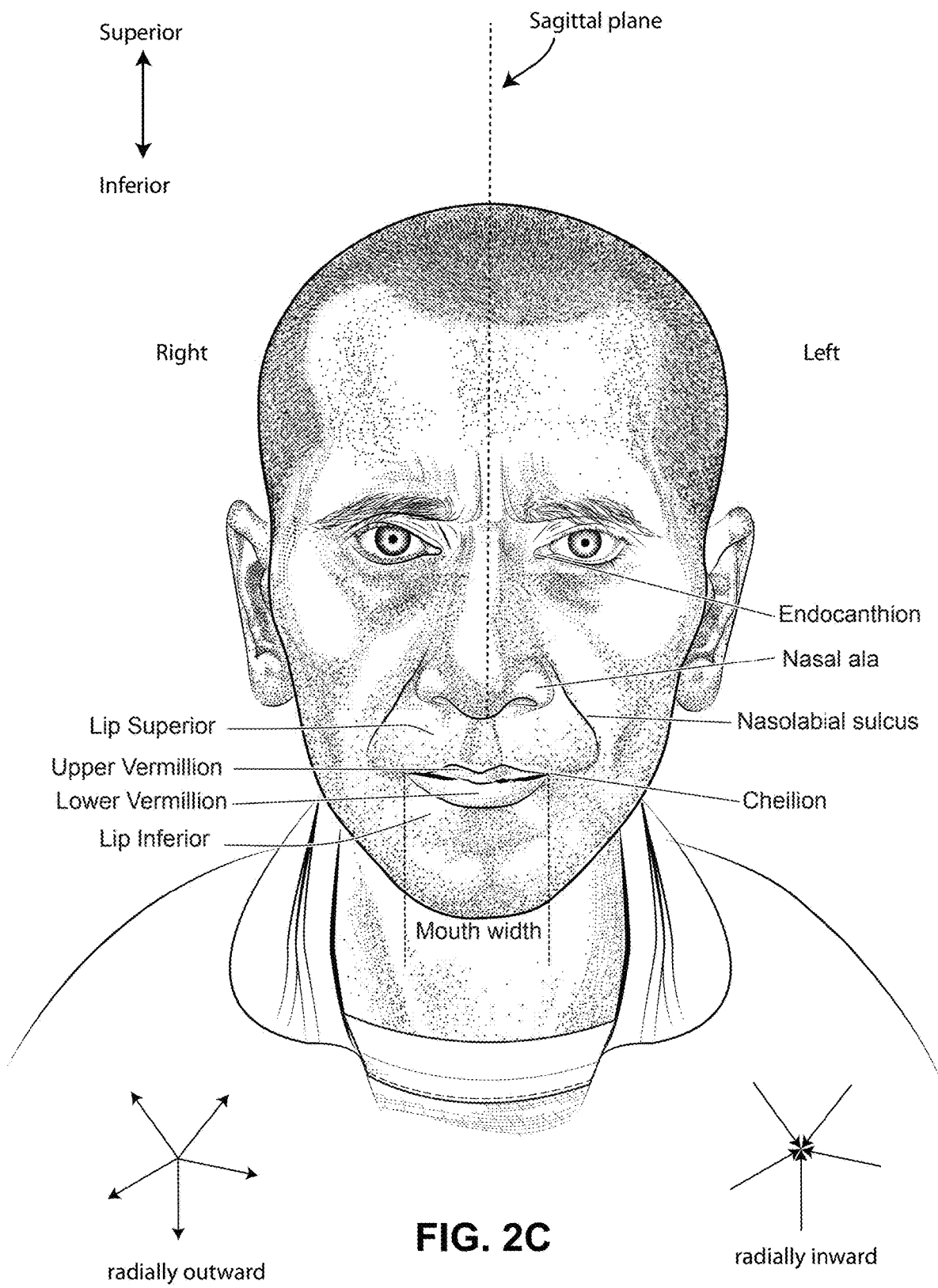

FIG. 2c is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
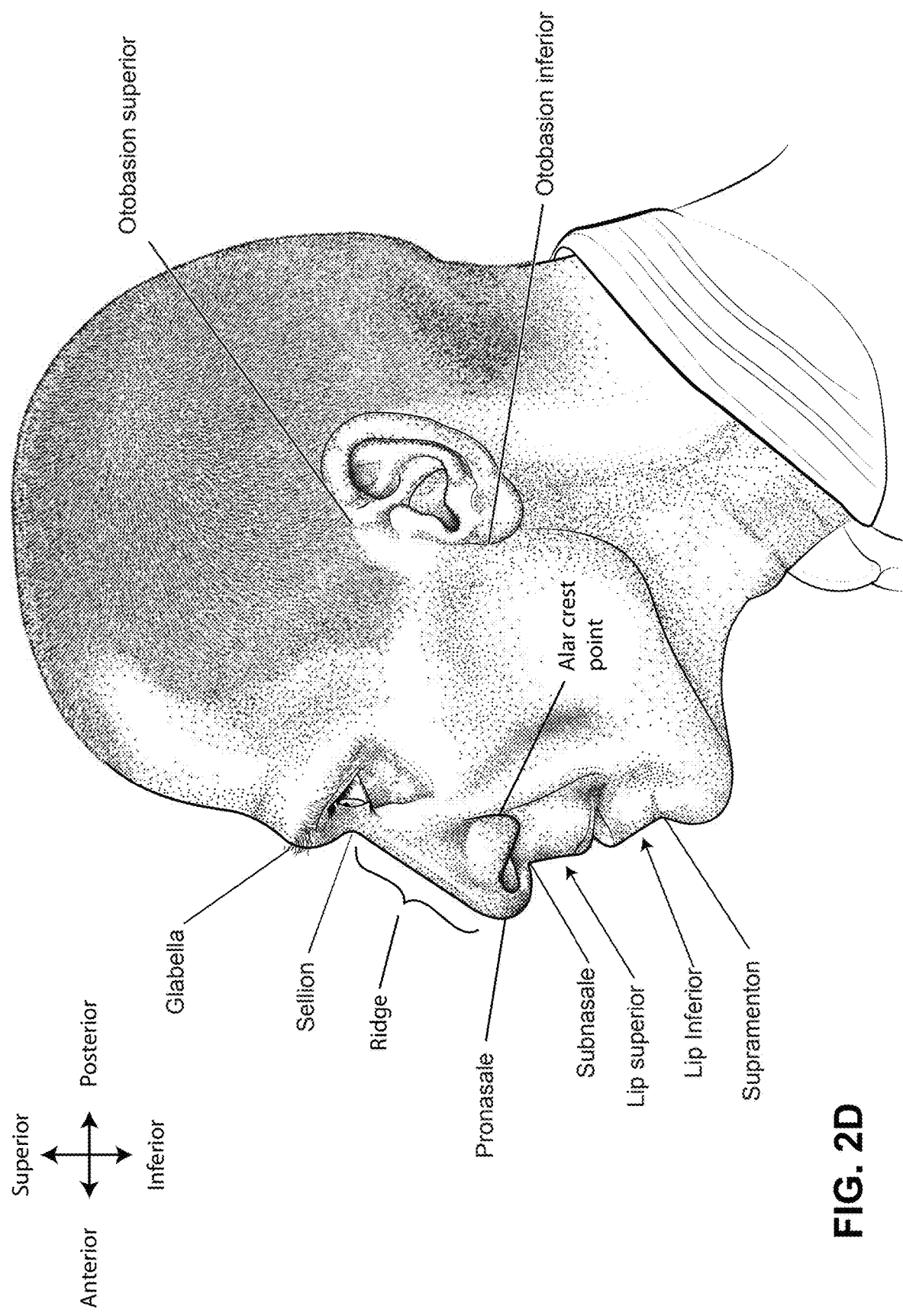

FIG. 2d is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
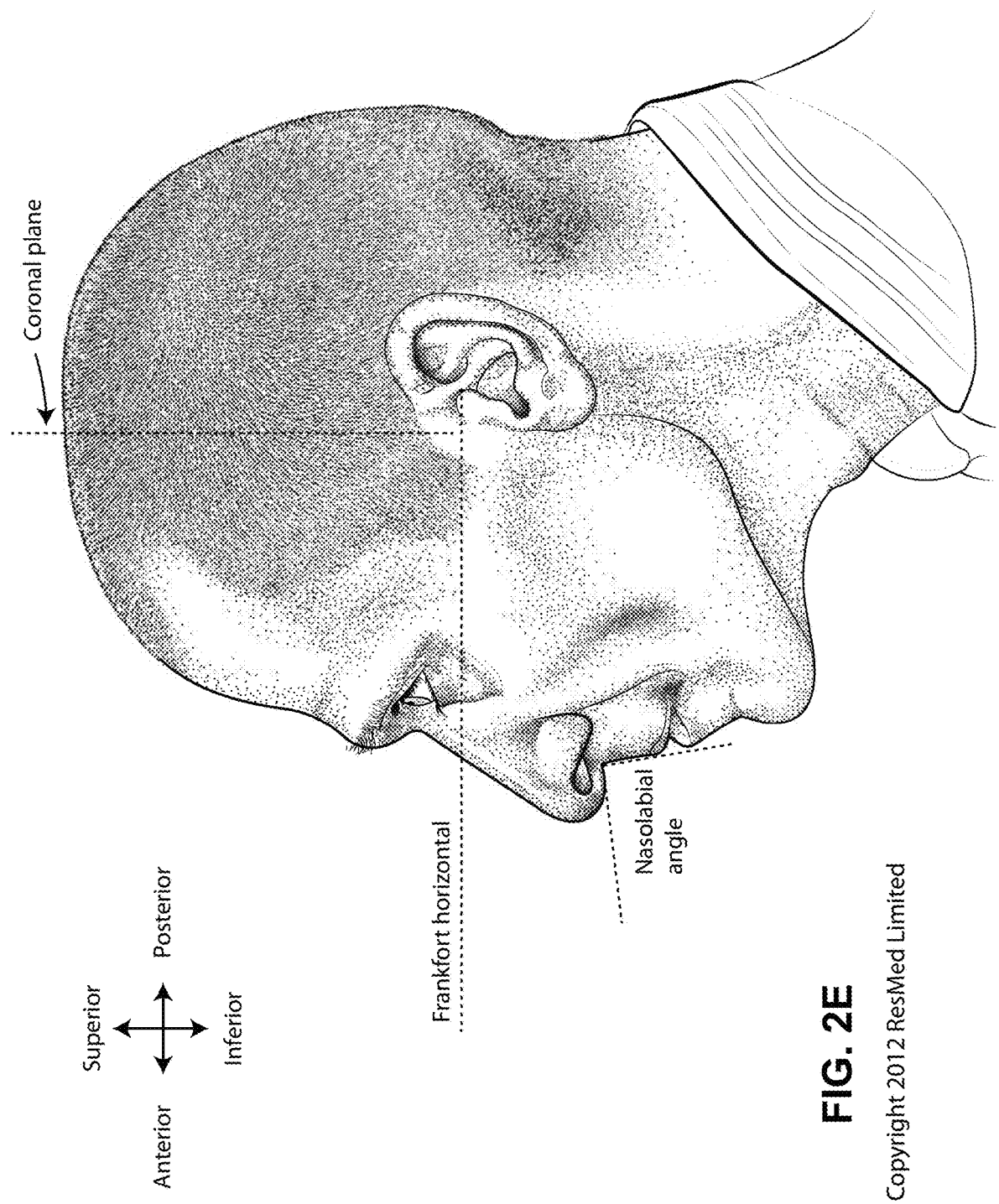

FIG. 2e is a further side view of a head. The approximate locations of the Frankfort horizontal and nasolabial angle are indicated. The coronal plane is also indicated.

Figure 2F:
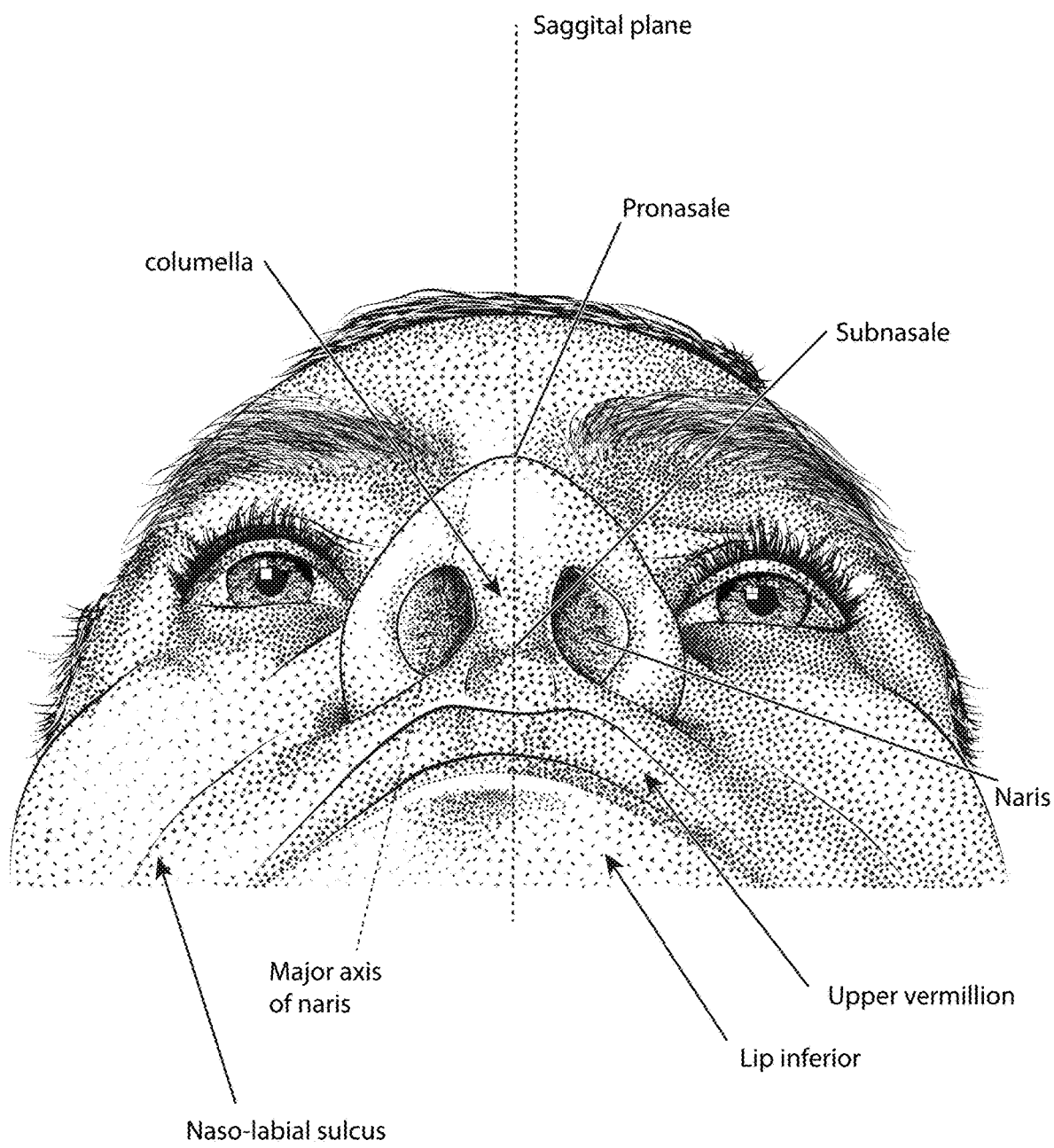

FIG. 2f shows a base view of a nose with several features identified including naso-labial sulcus, lip inferior, upper Vermilion, naris, subnasale, columella, pronasale, the major axis of a naris and the sagittal plane.

FIG. 2g shows a side view of the superficial features of a nose.

FIG. 2h shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2i shows a medial dissection of a nose, approximately several millimeters from a sagittal plane, amongst other things showing the septum cartilage and medial crus of greater alar cartilage.

FIG. 2j shows a front view of the bones of a skull including the frontal, nasal and zygomatic bones. Nasal concha are indicated, as are the maxilla, and mandible.

FIG. 2k shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
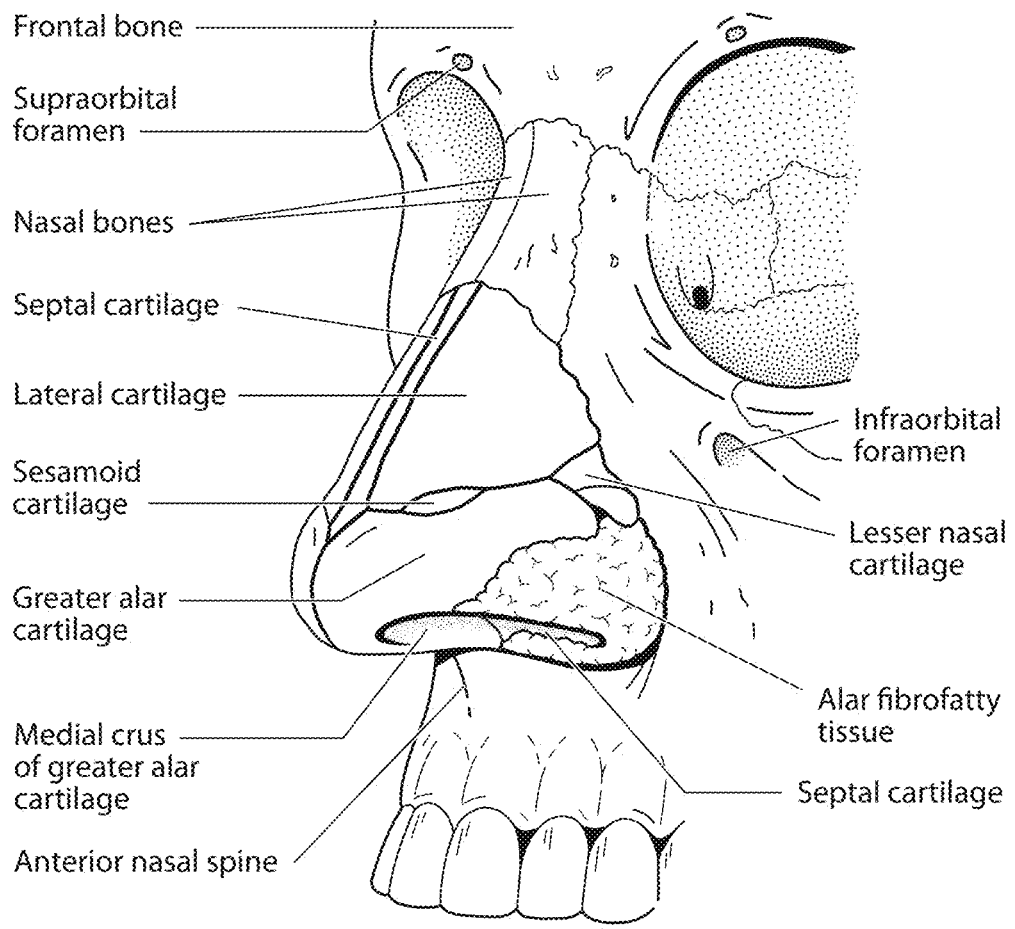

FIG. 2l shows an anterolateral view of a nose.

3.3 Patient Interface, Seal Forming Structure and Method of Manufacture

Figure 3A:
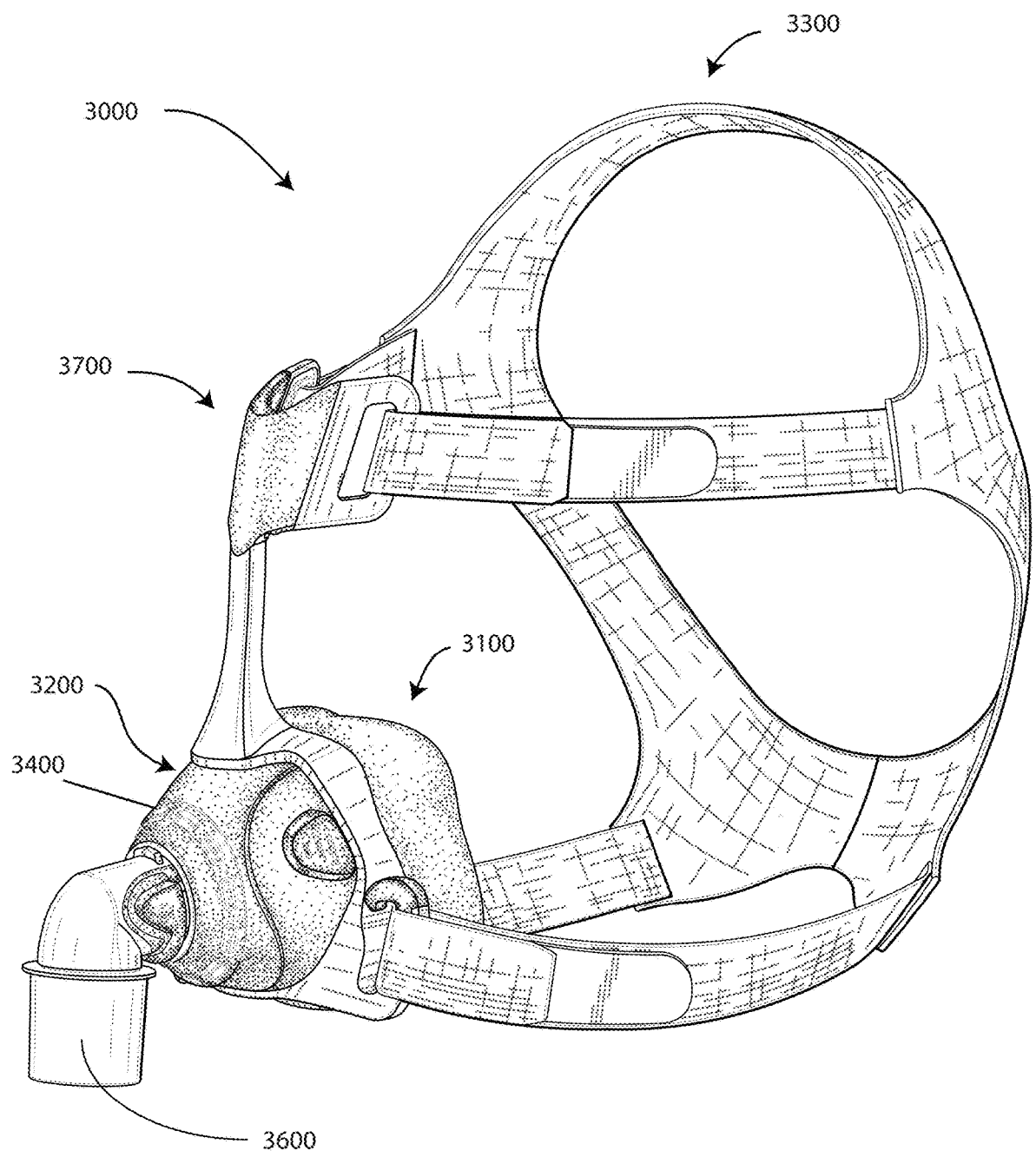

FIG. 3a shows a patient interface in the form of a nasal mask in accordance with one form of the present technology.

Figure 4B:
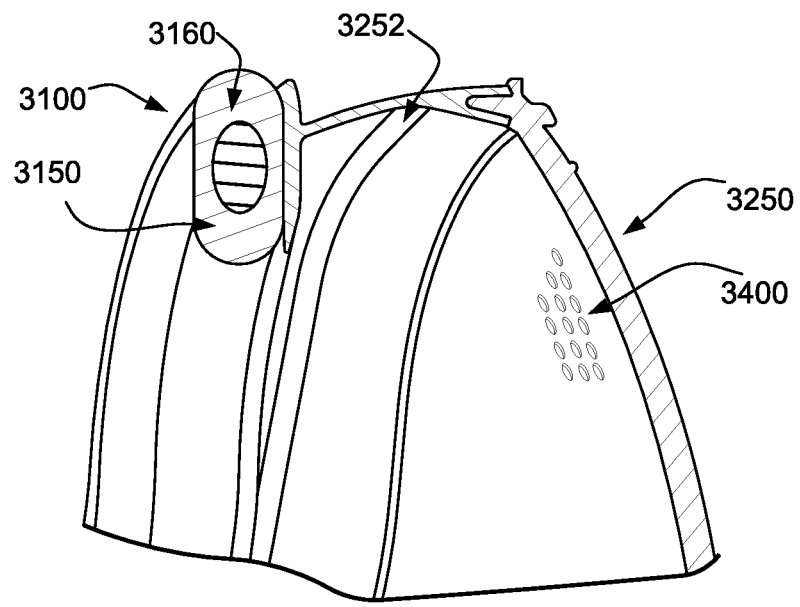
Figure 4A:
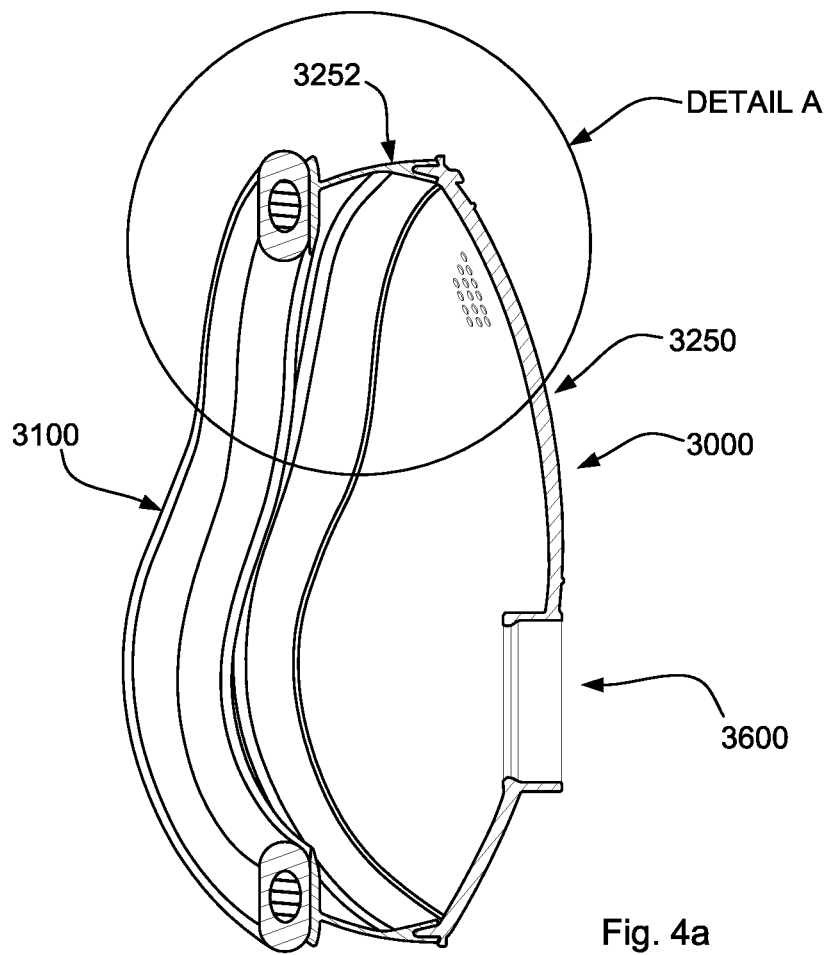

FIG. 4a shows a cross sectional view of patient interface in accordance with one form of the present technology.

FIG. 4b shows an enlarged detail of the patient interface of FIG. 4a.

Figure 5A:
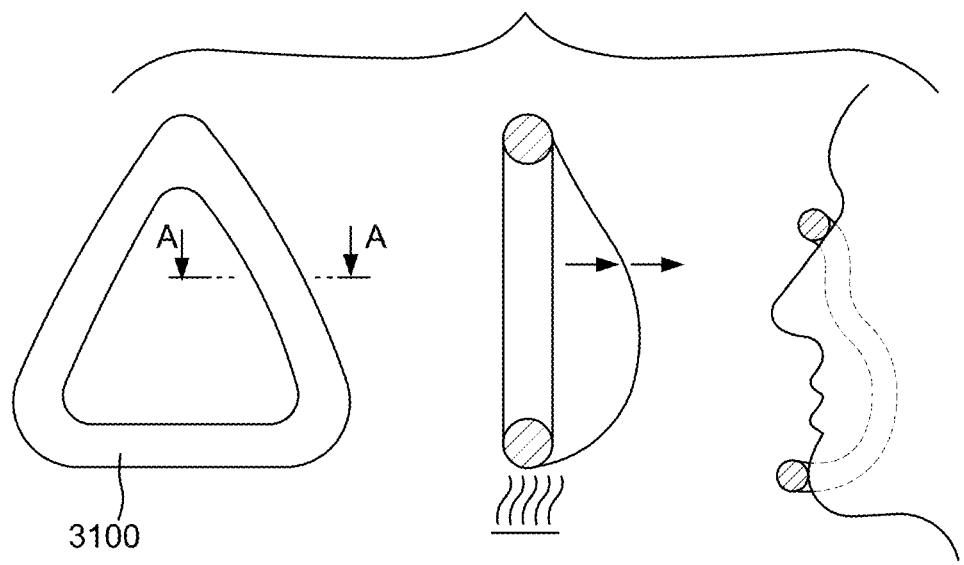
Figure 5B:
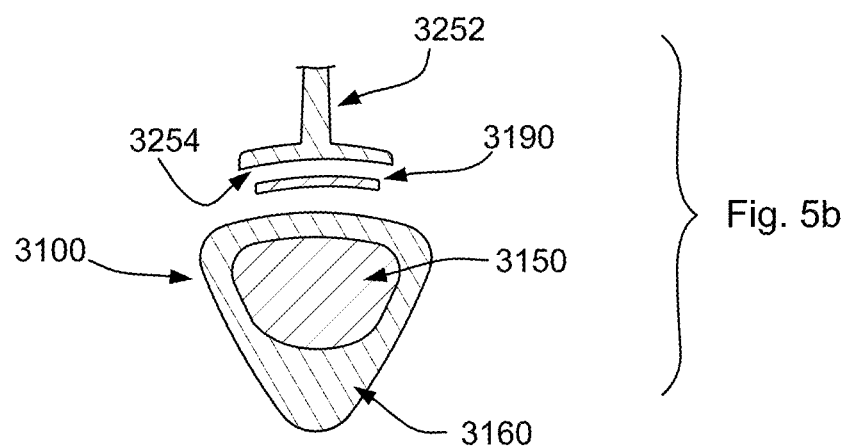
Figure 5C:
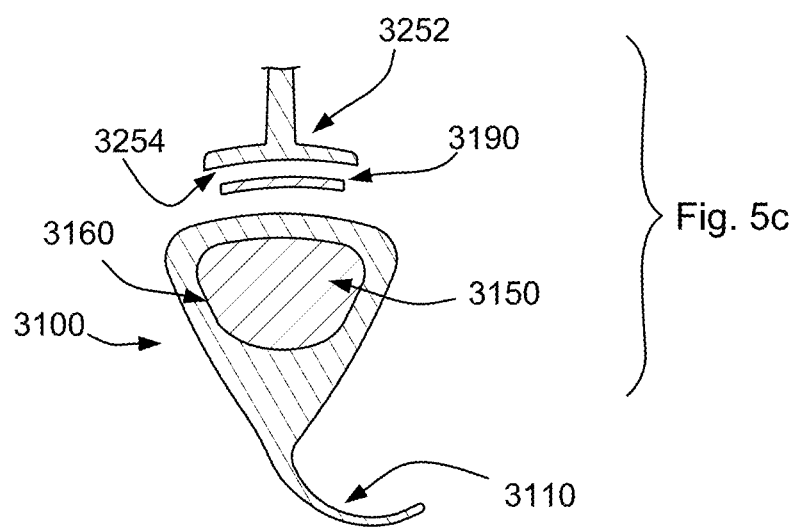

FIGS. 5a-5c show various aspects of patient interfaces in accordance with forms of the present technology.

FIGS. 6a-6g show still different aspects of patient interfaces in accordance with forms of the present technology.

FIGS. 7a-7c show still further aspects of patient interfaces in accordance with forms of the present technology.

Figure 8A:
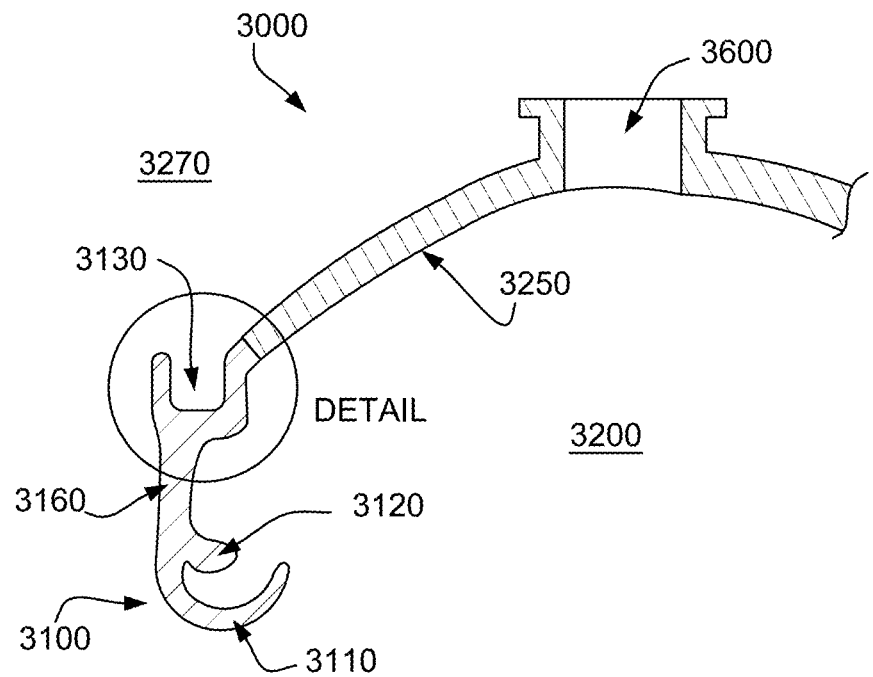
Figure 8B:
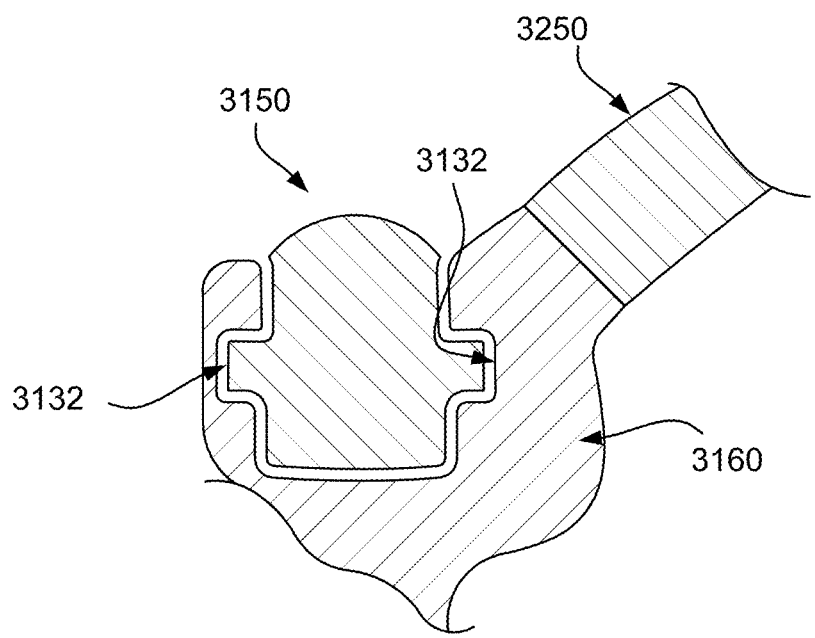

FIGS. 8a and 8b show still further aspects of patient interfaces in accordance with forms of the present technology.

Figure 9A:
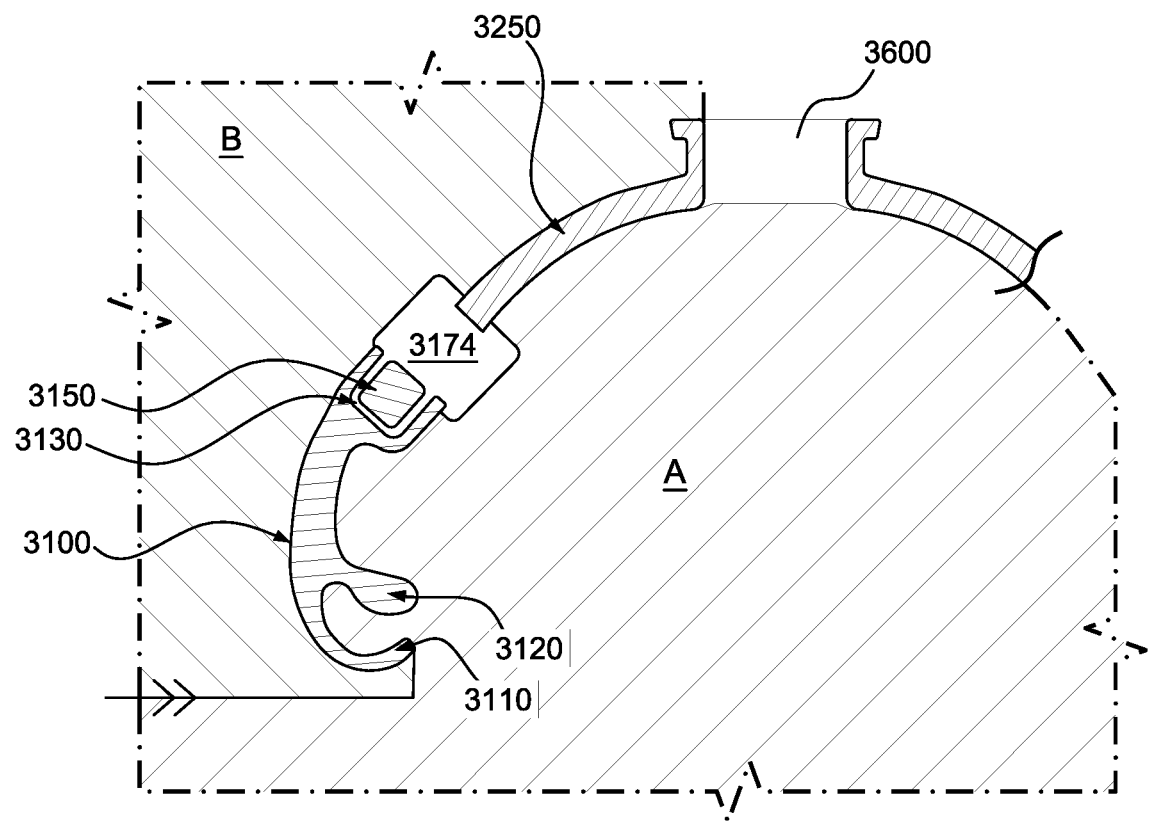

FIG. 9a shows a molding tool for manufacture of a patient interface in accordance with the present technology.

Figure 9B:
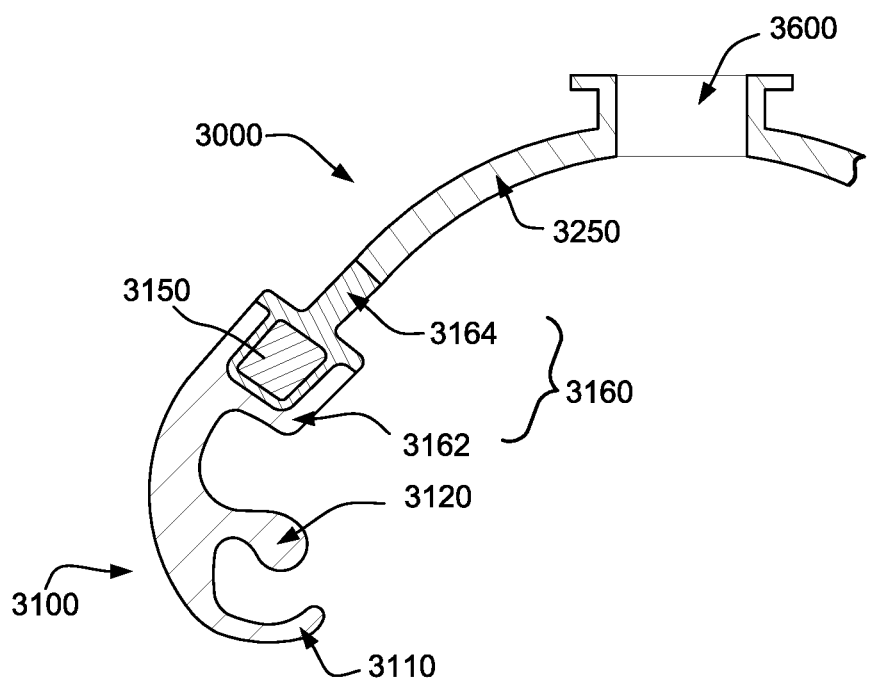

FIG. 9b shows a patient interface manufactured with the tool depicted in FIG. 9a.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 Patient Interface

A non-invasive patient interface 3000 in accordance with one aspect of the present technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange 3110 and a support flange 3120. The sealing flange 3110 comprises a relatively thin member with a thickness of less than about 1 mm, for example about 0.25 mm to about 0.45 mm, that extends around the perimeter 3210 of the plenum chamber 3200. Support flange 3120 may be relatively thicker than the sealing flange 3110. The support flange 3120 is disposed between the sealing flange 3110 and the marginal edge of the plenum chamber 3200, and extends at least part of the way around the perimeter 3210. The support flange 3120 is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

4.3.2 Plenum Chamber

The plenum chamber 3200 has a perimeter 3210 that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

4.3.3 Positioning and Stabilising Structure 3300

The seal-forming portion 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

4.3.4 Vent

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure 3500, e.g., a swivel.

4.3.5 Decoupling Structure(s)

In one form the patient interface 3000 includes at least one decoupling structure 3500, for example, a swivel or a ball and socket.

4.3.6 Connection Port

Connection port 3600 allows for connection to the air circuit 4170.

4.3.7 Forehead Support

In one form, the patient interface 3000 includes a forehead support 3700.

4.3.8 Anti-Asphyxia Valve

In one form, the patient interface 3000 includes an anti-asphyxia valve.

4.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

4.4 Further Description of Examples of the Patient Interface, the Seal Forming Structure and Manufacturing Methods FIG. 5a shows one aspect in accordance with the present technology. In this aspect of the present technology, a seal forming structure 3100 of a patient interface 3000 is provided. This seal forming structure 3100 may be a user formable pad preferably consisting of or comprising a thermo-formable material. In accordance with the center section/middle Figure of FIG. 5a, e.g., heat (depicted as wavy lines) may be applied to seal forming structure 3100, such that this seal forming structure 3100 softens. In this regard, it is pointed out that the present specification is in particular and preferably directed to a thermo-formable structure. However, even though the embodiments are directed thereto, the skilled person will understand that the present technology may also be employed be means of other user formable structures. The seal forming structure 3100 may then, in this softened state, be applied to a patient's face (see right depiction in FIG. 5a) and assume the approximate shape of the patient's face. When the seal forming structure 3100 cools down again, it will remain in this shape. Thereby, an individual or customized shape and thus fit of the seal forming structure on this particular user's face is achieved.

To achieve this, the seal forming structure 3100 may have a thermo-formable section 3150 (see, e.g., FIGS. 4a and 4b). This section may be made of a material having a specific transition temperature. Below this transition temperature, which may also be referred to as a melting temperature or as a softening point, the material maintains its shape. Above this transition temperature, the material may be deformed. Typically, this transition temperature is above the temperature a patient interface 3000 typically assumes in use. That is, this transition temperature may be, e.g., in the range of 40° C.-100° C. Lower temperatures of this range, such as 40° C. to 60° C. may be preferred to avoid to allow contact with a user's skin for customization without causing pain or skin damage to the face due to the material's temperature. As discussed, a user may heat the seal forming structure 3100 (either on its own or with the remainder of the patient interface 3000) above the transition temperature, e.g., by means of warm water, infrared radiation, microwave radiation or other means of heating available in the user's household and then deform the seal forming structure 3100. preferably by applying it to or pressing it on his or her face. When the seal forming structure 3100 then cools down again below the transition temperature, it will maintain the respective shape. As a result the seal forming structure may better fit to the patient's physiognomy of the face. Thus, a better sealing may be achieved and a more comfortable fit of the patient interface 3000 to the user.

This may be achieved in various embodiments of the present technology. Turning generally to FIG. 4a, a patient interface 3000 typically comprises a shell 3250. If the patient interface 3000 is realized as a mask, this shell 3250 may also be referred to as a chassis or as a mask chassis. The shell 3250 may be formed from a relatively rigid material, such as polycarbonate. However, other materials, such as polyamide, polybutylene terephthalate and/or others may also be used for this embodiment and the other embodiments of the present technology. Typically, the patient interface 3000 also comprises a connection port 3600 for connection to a breathing gas line. The connection port 3600 may either be adapted for direct connection of a breathing gas line or for indirect connection to such a breathing gas line, e.g., by means of a swivel elbow. The patient interface 3000 may also comprise a vent 3400 including a plurality of apertures for washing out a exhaled air. Furthermore, the embodiment depicted in FIGS. 4a and 4b also comprises a seal forming structure 3100, such as a pad. This seal forming structure 3100 includes the thermo-formable section 3150. The thermo-formable section 3150 may have a substantial oval shape in cross-section (see e.g., FIG. 4b). Thus, the thermo-formable section 3150 may have a substantially round shape, and have a first dimension (e.g., a horizontal dimension as shown in FIG. 4b) measured generally perpendicularly to a larger, second dimension (e.g., a vertical dimension as shown in FIG. 4b). The seal forming structure 3100 also comprises a second portion 3160 of another material. In the embodiment depicted in FIGS. 4a and 4b, this section of another material completely surrounds or encloses the thermo-formable section 3150, which may therefore also be referred to, in this embodiment, as a thermo-formable core section. Thus, the second portion 3160 may adapt a shape that is substantially the same as the thermo-formable section 3150. In other words, the second portion 3160 may also have a substantially oval shape. However, the second portion 3160 may have a pair of sides that are substantially straight (e.g., as opposed to curved), and may be substantially parallel to the second dimension. As depicted, the second section 3160 is adapted to come into contact with a patient's face (e.g., via one of the substantially straight sides) during use of the patient interface 3100. Typically, the second section 3160 is therefore preferably formed of a skin-friendly and/or seal enhancing material, such as, for example, silicon. In the depicted embodiment, the patient interface also comprises a carrier portion 3252 or cushion structure. One end of the carrier portion 3252 may be T-shaped. The carrier portion 3252 may be formed integrally with shell 3250. However, alternatively, carrier portion 3252 may also be formed from another material than shell 3250. For example, carrier portion 3252 may also be formed of a material being more resilient then shell 3252 to allow, e.g., for bending of the carrier portion 3252. As depicted in FIG. 4b, carrier portion 3252 may have a T-shaped end section— also see FIGS. 5b and 5c being sections along line A-A of FIG. 5a. Such an end section may include a platform region 3254 (preferably the T-beam of the T-shape cross sectional structure), which may be generally flat. The seal forming structure 3100 may be applied to this platform region 3254, e.g., by means of an adhesive such as an adhesive strip 3190, so that the other substantially straight side contacts the platform region 3254. In this regard, seal forming structure 3100 may also have a substantially flat end section to allow for easy connection to platform region 3254 by means of adhesive 3190.

FIGS. 5b and 5c depict the cross-section of different embodiments. The main difference of the two embodiments depicted in FIGS. 5b and 5c resides in the fact that the seal forming structure 3100 of the embodiment in FIG. 5c includes a sealing flange 3110. This sealing flange 3110 may also be referred to as a sealing membrane or as a sealing lip. This sealing flange 3110 is a structure comprising, in a cross sectional view as depicted in FIG. 5c, an elongation which is substantially larger than its thickness. In this regard, the sealing flange 3110 may also be referred to as being a thin section. The sealing flange 3110 may allow for a particularly safe and comfortable seal between the patient interface and the user's face. As depicted, the sealing flange 3110 is formed integrally with the second section 3160. That is, in other words, the sealing flange 3110 is formed as a part of this second section 3160.

As discussed, in the embodiments depicted in FIGS. 4 and 5, the thermo-formable section 3150 may be completely enclosed by, surrounded by or embedded within the second section 3160. In other words only the second material of section 3160 of seal forming structure 3100 may be exposed to the outside. In again other words, a patient using this patient interface may only come into contact with second section 3160, but not with the thermo-formable section 3150. This may be beneficial, as the patient, when handling seal forming structure 3100, would only come into contact with the section 3160, which may be generally formed of skin-friendly material. This may broaden the choice of thermo-formable materials to be used for thermo-formable section 3150. Furthermore, it may also give the patient a more comfortable feel of the seal forming structure 3100, as the patient only comes into contact with materials, which are already known to him. In particular, this may also improve patient compliance.

Still further aspects of the embodiment depicted in FIG. 5a to FIG. 5c may include that the seal forming structure 3100, e.g., a user formable pad, may be applied to a carrier portion 3252, that is a carrier system, preferably by means of adhesive. The shaping of the seal forming structure 3100 will transfer to the carrier system by deforming the respective component. Prior to forming, the seal forming structure 3100 may be substantially flat and shaped suitable to correspond to the carrier portion 3252. This may also include the additional advantages of the respective seal forming structure 3100 being replaceable and enabling an upgrade of existing patient interfaces.

The present technology, however, is not limited to the embodiment depicted in FIGS. 4 and 5. Another preferred embodiment of the present technology is also depicted in FIGS. 6a to 6g. FIG. 6a again depicts the general outline of a patient interface 3000 including a shell or chassis 3250 and a seal forming structure 3100. Again, a connection portion 3600 for connection of a tube or an elbow is included. FIG. 6b depicts a cross-sectional view along line A-A of FIG. 6a. It should be noted that FIGS. 6a and 6b (as well as FIGS. 6c to 6e) depict a patient interface 3000 (or parts/details thereof) during the manufacturing process, that is before the patient interface is ready for use by a patient. In particular, the seal forming structure 3100 is not yet completely formed in these FIGS. 6a to 6e. To the contrary, in these Figures, the patient interface 3000 to be formed includes the shell 3250 and the thermo-formable section 3250 of seal forming structure 3100. The shell 3250 and the thermo-formable section 3150 may be connected to each other in a variety of ways, as depicted in FIGS. 6c to 6e. According to FIG. 6c, there may be provided an interface 3256 shaped to support a chemical bond between the thermo-formable section 3150 and the shell 3250, such interface may be a projection. In the embodiments discussed in conjunction to FIGS. 6a to 6g, the respective section of the shell 3250 may also be referred to as a substrate, onto which the thermo-formable section 3150 is applied. According to FIG. 6d, there may also be provided a molded mechanical interlock 3258 for connection of the shell or substrate 3250 and the thermo-formable section 3150. This may be achieved by provision of a grid like structure comprising holes between structural sections 3258. Furthermore, the tool sections may also be connected to each other by means of a mechanical interlock 3260, such as a snap fit, as depicted in FIG. 6e. However, as will be apparent, the skilled person may also use other means to interconnect the substrate 3250 and the thermo-formable section 3150.

As depicted (see, e.g., FIG. 6b) the thermo-formable section 3150 may have a generally elongated shape. That is, in a cross sectional view, one dimension of the thermo-formable section may be substantially larger than another dimension. In this regard, the thermo-formable section 3150 may be thin. In other words, the thermo-formable section 3150 may also be referred to as a fin 3150.

In other words, and as described above and below, the
FIG. 6a shows a frontal view of a mask chassis with a thermoformable fin around the entire circumference, FIG. 6b a cross section of same. FIGS. 6c to 6e illustrate different details of means of connection between chassis and thermoformable fin. FIG. 6f shows a chassis and thermoformable fin (which may use any of the principles, e.g. as shown in and discussed with regard to FIGS. 6c to 6e) overmoulded in silicone to form a mask cushion. FIG. 6g shows a detail of a cross sections of the thermoformable fin deformed after the adaption process.

As discussed, FIGS. 6a-6e depict the patient interface 3000 in an intermediate state of the production process. In addition to the structures discussed above in conjunction to FIGS. 6a-6e, a second material is applied to the patient interface 3000 to form the second section 3160 of seal forming structure 3100, here not simply a pad but a cushion-structure. In this context, it should be noted that the general discussion of a pad includes reference to a cushion and vice-versa. Again, typically a material suitable for skin contact, that is skin-friendly material may be used for the material of the second section 3160. As an example, silicon may be used.

Generally, this second section 3160 of seal forming structure 3100 may be applied to the other parts by means of over molding. That is, the two component part depicted in FIGS. 6a-6e may be inserted into a tool for over molding and may be over molded, e.g., with silicon, to form the seal forming structure 3100, such as the pad or cushion. Thus, a three component (3K) patient interface would be formed with a thermo-formable element.

After formation of the patient interface 3000 in such a way, the user may heat up the patient interface 3000 to soften the thermo-formable section or thermo-formable element 3150 and apply it to the face so that this element may take shape. The thermo-formable section, that is, in this embodiment, the thermo-formable fin, may also be (pre-)shaped to match a patient's generalized physiognomy quite closely, thereby limiting the amount of shaping required to achieve the adaptation to individual features. As indicated above, FIG. 6f shows a preferred structure before heating and customization while FIG. 6g shows the same preferred structure after thermoforming.

Figure 6A:
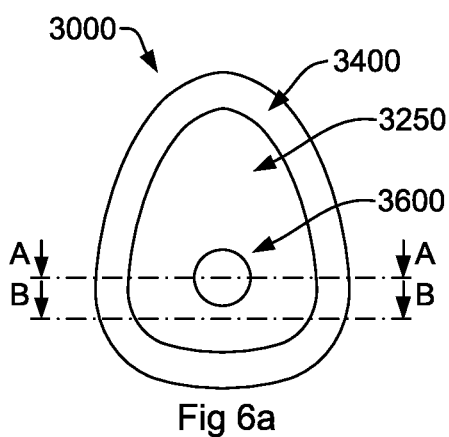
Figure 6B:
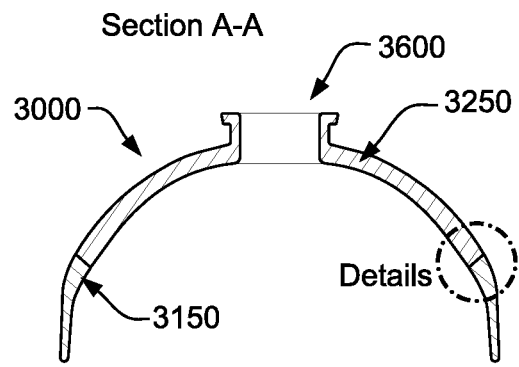
Figure 6C:
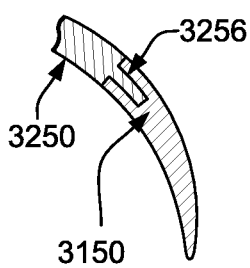
Figure 6D:
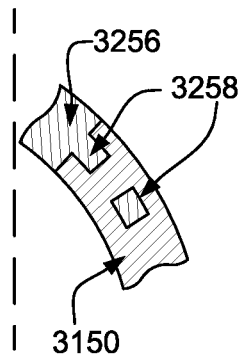
Figure 6E:
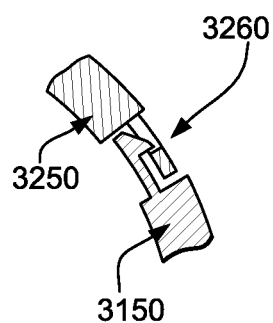
Figure 6F:
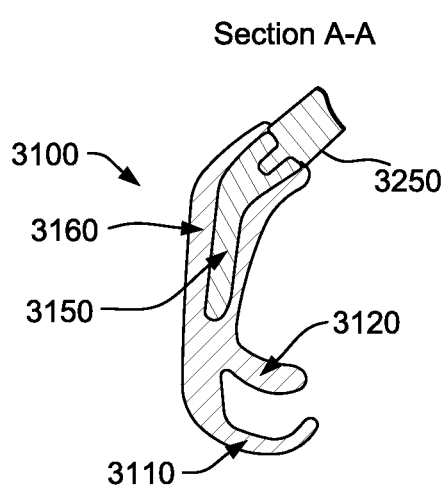
Figure 6G:
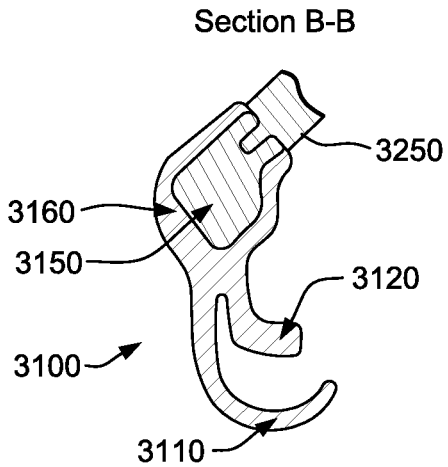

FIGS. 6f and 6g show two cross sectional views along, e.g., lines A-A and B-B (which are basically identical cross sections but simply refer to different points in time, i.e. one before A-A and one after thermoforming B-B) of FIG. 6a, however, only after over-molding with a second material. While FIG. 6a shows the structure before thermoforming, FIG. 6b shows the structure after shaping by a patient has taken place. As will be apparent, the part of the thermo-formable section 3150 in FIG. 6g has been deformed vis-à-vis the former state of the thermo-formable section 3150 as seen in FIG. 6f. While the part of the thermo-formable section 3150 in FIG. 6f has a thin, fin-like shape, the part of the thermo-formable section 3150 in FIG. 6g has been compressed to adopt a more bulky cross-sectional shape. That is, in other words, the amount of forming required may not be uniform around the perimeter of the patient interface. Instead, there may be areas with more deformation and/or deflection and other areas with less deformation and/or deflection.

Furthermore, FIGS. 6f and 6g also depict the seal forming structure 3100 to comprise both a sealing flange 3110 and a support flange 3120. These may be formed integrally with the second section 3160. In other words, these sections may also be referred to be part of the second section 3100, that is, in other words, the second section 3160 comprises the sealing flange 3110 and the support flange 3120. However, the skilled person will readily understand that the provision of sealing flange, e.g. membrane 3110 and undercushion 3120, in this embodiment is only exemplary—that is, the skilled person may also not include these features in the present embodiment or may, alternatively, include the features of a sealing flange 3110 and a support flange 3120 in the other embodiments, such as the embodiment depicted in FIGS. 4a to 5b.

As is also depicted in FIGS. 6f and 6g, the thermo-formable material 3150 may be completely surrounded by other material. That is, all the surface sections of the thermo-formable section 3150 not being in contact with substrate 3250 are in contact with second section 3160 of seal forming structure 3100. In other words, no portion of the thermo-formable section 3150 is exposed to ambient, such that the user will not come into contact with thermo-formable section 3150, such that the user only comes to contact with material he is used tom, which may improve, e.g., user compliance. In other words, as depicted and discussed, part of the thermo-formable material may not be covered or surrounded by second material or section 3160 of seal forming structure 3100 but in contact with and covered by substrate 3250.

FIGS. 7a to 7c depict yet another embodiment of the present technology. Again, FIGS. 7a and 7b depict the patient interface 3100 before the final step of over molding and FIG. 7c depicts the patient interface 3000 after over-molding has taken place. According to FIG. 7a, the patient interface 3000 to be formed includes a shell or chassis 3250 with a connection port 3600 (also see the sectional view of FIG. 7b). Furthermore, the patient interface 3000 again comprises a thermo-formable section 3150. The thermo-formable section 3150 includes a perimeter section 3152 and a plurality of leg members or web portions 3154 connecting the perimeter section 3152 to the mask shell 3250. In the depicted embodiment, there are provided three web portions 3154, however, the skilled person will understand that also a different number of web portions 3154, such as 2, 4, 5 or more web portions may be provided. The web portions 3154 are preferably also made of the thermo-formable material, but may also be made of another material.

FIG. 7c again depicts a cross sectional view along line A-A of FIG. 7a after over molding has taken place. As will be apparent, this embodiment, too, comprises a seal forming structure 3100 including a thermo-formable section 3150 and a second section 3160. As discussed above, the second section 3160 may include a sealing flange 3110 and may include a support flange 3120. Again, the patient interface may be formed in such a way that no section of the thermo-formable section 3150 is exposed to ambient, but the thermo-formable section 3150 is completely enclosed by the shell 3250 (at the connection points) and by the second section 3160 of the seal forming structure 3100.

In this embodiment, the thermo-formable section is not connected or bonded to the shell 3250 (or substrate) around the entire perimeter, but only in selected locations, e.g., at the web portions 3154. This may improve the forming range of the user formable seal forming structure 3100. In other words, the thermo-formable section 3150, which may also be fin-shaped, may protrude further away from the shell 3250, thereby adding additional degrees of freedom to the shaping. As discussed, the perimeter section 3150 may be in the shape of a fin, however, it may also take another shape and be referred to as a frame or stiffener portion 3152. In the cross sectional view of FIG. 7b, it can be seen that in the lower half of this cross sectional view, there is no direct connection between the thermo-formable section 3150 and the shell or substrate 3250. Instead, the gap G of FIG. 7b is filled with the material of the second section 3160, such as silicon, during the over molding process, resulting in a larger extension of the second section 3160 contributing to a larger adjustment range.

FIGS. 8a and 8b show another embodiment of the present technology, FIG. 8b being an enlarged view of a detail of FIG. 8a. Again, the patient interface 3000 of this embodiment includes a shell or chassis 3250 with a connection port 3600. Furthermore, the patient interface 3000 also includes a seal forming structure 3100, which may include a sealing flange 3110 and which may also include a support flange 3120, as discussed above (although these structures do not necessarily need to be provided).

Furthermore, the seal forming structure 3100 includes a pocket or groove 3130 adapted for receiving a thermo-formable section 3150. Generally, the shell 3250 and the seal forming structure 3100 define together a plenum chamber 3200. During use, seal forming structure 3100 and shell 3250 limit, together with a patient's face, a certain space, that is the plenum chamber 3200. This section may also be referred to as the interior of the patient interface. Conversely thereto, there is also an exterior 3270 of the patient interface 3000. That is the space other the space delimited, during use, by the patient interface 3000 and the patient. Preferably, the groove or pocket 3130 is only accessibly from the patient interface's outside 3270. In other words, the pocket or groove 3130 is provided on the outside 3250 of the patient interface 3000. As depicted in FIG. 8b the groove 3130 may be provided with at least one undercut 3132 and preferably a plurality of undercuts 3132, that is, e.g., two undercuts 3132, forming a mechanical interlock feature to prevent the thermo-formable section 3135 from coming loose during forming. Alternatively or in addition, a chemical bond can be formed between the thermo-formable section 3150 and the groove 3130.

For production of this embodiment of the present technology, the shell or chassis 3250 and the section 3160 of the seal forming structure 3100 are molded in a two component molding process in such a way that the seal forming structure 3100 includes the groove or pocket 3130 into which thermo-formable material is introduced at a second stage after the molding, e.g., by means of potting and/or dosing processes. Again, the section 3160 of the sealing structure may be silicon and the thermo-formable material may be polycaprolactone (PCL).

This embodiment allows for an alternative manufacturing process, which is particularly easy and allows a simple introduction of the thermo-formable section 3130.

A still further embodiment of a patient interface 3000 of the present technology, as well as a corresponding manufacturing process, are depicted in FIGS. 9a and 9b. FIG. 9a depicts a manufacturing tool, such as a molding tool with two sections A and B. One of the two sections A and B is a movable section, while the other section is a fixed section of the tool. For example, section B may be a fixed tool section and section A may be a movable tool section. In this tool, there is placed an insert for a shell 3250 of the patient interface 3000 having a connection portion 3600. Furthermore, there is also placed an insert for the seal forming structure 3100 in this tool. Furthermore, an insert of thermo-formable material 3150 is also placed in this tool. Near and around the insert for the thermo-formable section 3150, there is provided a gap of cavity 3174. In particular, the insert for the seal forming structure 3100 may include a pocket or cavity 3130 into which the insert of thermo-formable material 3150 is placed.

The thermo-formable material 3150 may be cast, pointed or dosed or molded into the groove 3130 or assembled as a separate component thereof. The resulting two-component-structure may be inserted into the tool A-B, together with the insert for the shell or chassis 3250. All these components may then be over molded in another step to complete the assembly. That is, a further material, such as silicon, is introduced to fill the cavity 3174 to connect the components with each other, so that the seal forming structure 3100, the thermo-formable material 3150, and the shell 3250, which form a resulting patient interface 3000, are integrally formed. The seal forming structure 3100, the thermo-formable material 3150, and the shell 3250 are permanently fixed in this one piece construction.

A resulting patient interface 3000 is depicted in cross section in FIG. 9b. Again, this patient interface includes a shell or chassis 3250 with a connection port 3600, as well as a seal forming structure 3100, which may (or may not) comprise at least one of a sealing flange 3110 and a support flange 3120. Furthermore, the seal forming structure 3100 comprises a thermo-formable section 3150 and a second section 3160 of another material. The second section 3160 includes a first sub section 3162 and a second sub section 3164. Again, this second section may include the sealing flange 3110 and the support flange 3120. Furthermore, the seal forming structure 3100 of this embodiment also includes the second sub section 3164 integrally connecting the seal forming structure 3100 to the shell 3250. However, even though the structure 3160 is depicted to be a structure separate from the connecting structure 3164 of seal forming structure 3100, these sections may be made of the same material, such as silicon. However, alternatively, these sections may also be made from different materials.

This embodiment may allow for still another manufacturing process and a simple molding process, as well as simplicity of tooling.

4.5 Glossary

For the purposes of the present technology disclosure, in certain forms of the present technology, one or more of the following definitions may apply. In other forms of the present technology, alternative definitions may apply.

4.5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: CPAP therapy will be taken to mean the application of a supply of air to an entrance to the airways at a pressure that is continuously positive with respect to atmosphere. The pressure may be approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

4.5.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.5.3 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 4.5.4 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.5.5 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.5.6 Materials

Silicone or Silicone Elastomer: A synthetic rubber. In this specification, a reference to silicone may be a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

4.5.7 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie: A tie will be taken to be a structural component designed to resist tension.

Vent: (noun) the structure that allows an intentional flow of air from an interior of the mask, or conduit to ambient air, e.g. to allow washout of exhaled gases.

4.5.8 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:
Readily conforming to finger pressure.
Unable to retain its shape when caused to support its own weight.
Not rigid.
Able to be stretched or bent elastically with little effort.
The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during respiratory pressure therapy.

4.6 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Any relative term, such as "generally", "substantially", "about", etc. preceding a respective feature should be understood to also encompass the respective features within its exact sense, unless stated otherwise. That is, e.g., "about 3 elements" also encompasses "(exactly) 3 elements" and "generally vertical" also encompasses "vertical".

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. Method of manufacturing a patient interface for treatment of sleep disordered breathing using air pressure by delivery of air to a patient's airway, the method comprising:
    locating a shell, a first sub section of a seal forming structure, and a first section of the seal forming structure in a tool, wherein the first sub section includes a first end with at least one flange and a second end that includes a groove, and wherein the first section is constructed from a thermoformable material;
    subsequently introducing a moulding material to the tool and overmoulding the shell, the first sub section, and the first section, wherein the moulding material forms a second sub section of the seal forming structure that connects the first sub section to the shell and fully encloses the first section within the groove; and
    locating the first section in the groove along an insertion axis prior to moulding, wherein the insertion axis does not intersect the at least one flange.

2. The method of claim 1, further comprising casting or moulding the first section into the groove of the first sub section.

3. The method of claim 1, further comprising assembling the first section separately from the first sub section.

4. The method of claim 1, further comprising positioning the shell apart from the first section to form a gap prior to introducing the moulding material.

5. The method of claim 1, wherein the first sub section and the second sub section are constructed from the same material.

6. The method of claim 5, wherein the first sub section and the second sub section are constructed from silicone.

7. The method of claim 1, wherein the first sub section and the second sub section are constructed from different materials, each of which is different than the thermoformable material.

8. The method of claim 1, wherein the second sub section extends between the first sub section and the shell.

9. The method of claim 1, wherein the second sub section is partially received within the groove and around the first section.

10. The method of claim 1, wherein the first sub section includes a sealing flange and a support flange.

11. The method of claim 1, wherein the shell is formed from a rigid material.

12. The method of claim 1, wherein after overmoulding, the seal forming structure, the thermoformable material, and the shell are permanently fixed in this one piece construction.

13. A patient interface for treatment of sleep disordered breathing using air pressure by delivery of air to a patient's airway, the patient interface comprising a shell and a seal forming structure, wherein the seal forming structure comprises a first section of a thermoformable material and a second section of another material, wherein the second section comprises different sub sections, wherein a first sub section includes a first end with at least one flange and a second end with a groove, and wherein the first section is located in the groove along an insertion axis by means of a second sub section, the second sub section connecting the seal forming structure to the shell and fully enclosing the first section within the groove, wherein the shell and the second sub section are integrally formed together to form a one piece construction, and wherein the insertion axis intersecting the shell and not intersecting the at least one flange.

14. The patient interface of claim 13, wherein the at least one flange includes a sealing flange configured to contact the patient and a support flange having a greater thickness than the sealing flange for supporting the sealing flange, and wherein the insertion axis intersects neither the support flange nor the sealing flange.

15. The patient interface of claim 13, wherein the second sub section extends between the first sub section and the shell.

16. The patient interface of claim 13, the second sub section is partially received within the groove and around the first section.

17. The patient interface of claim 13, wherein the second sub section is overmoulded onto the shell.

18. The patient interface of claim 13, wherein the first sub section and the second sub section are each constructed from a different material than the first section.

\* \* \* \* \*